United States Patent
Perschbacher et al.

(10) Patent No.: US 8,929,981 B2
(45) Date of Patent: *Jan. 6, 2015

(54) METHODS AND SYSTEMS FOR IDENTIFYING AND USING HEART RATE VARIABILITY AND HEART RATE VARIATION

(71) Applicant: Cardiac Pacemakers, Inc., St. Paul, MN (US)

(72) Inventors: David L. Perschbacher, Coon Rapids, MN (US); Arjun D. Sharma, St. Paul, MN (US); Craig Stolen, New Brighton, MN (US); Kira Q. Stolen, New Brighton, MN (US); Milan Seth, Minneapolis, MN (US); Paul W. Jones, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/707,204

(22) Filed: Dec. 6, 2012

(65) Prior Publication Data

US 2013/0150912 A1 Jun. 13, 2013

Related U.S. Application Data

(60) Provisional application No. 61/569,350, filed on Dec. 12, 2011, provisional application No. 61/643,767, filed on May 7, 2012.

(51) Int. Cl.
| | | |
|---|---|---|
| *A61N 1/36* | (2006.01) | |
| *A61B 5/024* | (2006.01) | |
| *A61N 1/365* | (2006.01) | |
| *A61B 5/11* | (2006.01) | |
| *A61B 5/00* | (2006.01) | |

(52) U.S. Cl.
CPC ......... *A61N 1/36592* (2013.01); *A61N 1/36507* (2013.01); *A61N 1/36535* (2013.01); *A61B 5/02405* (2013.01); *A61B 5/1116* (2013.01); *A61B 5/7275* (2013.01); *A61N 1/36585* (2013.01)
USPC .......................................... 607/18

(58) Field of Classification Search
None
See application file for complete search history.

(56) References Cited

U.S. PATENT DOCUMENTS

| | | | |
|---|---|---|---|
| 5,101,824 A | | 4/1992 | Lekholm |
| 5,309,919 A | * | 5/1994 | Snell et al. ..................... 600/510 |

(Continued)

FOREIGN PATENT DOCUMENTS

| | | |
|---|---|---|
| WO | WO-2013090118 A2 | 6/2013 |
| WO | WO-2013090118 A3 | 11/2013 |

OTHER PUBLICATIONS

"How Evolving Sensor Technology and Rate-Responsive Pacing Can Improve Clinical Outcomes in CI," [Online]. Retrieved from the Internet: <http://www.medscape.org/viewarticle/724645?src=emailthis>, (Jul. 19, 2010), 26 pgs.

(Continued)

*Primary Examiner* — Paula J Stice
(74) *Attorney, Agent, or Firm* — Schwegman Lundberg & Woessner, P.A.

(57) ABSTRACT

A heart rate variability or heart rate variation can be identified using sensed and/or paced heart beats. One or more patient metrics, such as a variability index or a variation index, can correspond to the identified heart rate variability or heart rate variation. The patient metrics can be used to identify a need for a particular therapy, such as a rate-responsive pacing therapy. The patient metrics can be used to identify patients at an elevated risk of death. Methods and systems to identify therapy indications or at-risk patients are provided. In an example, a patient risk profile can be adjusted, such as in response to an identified patient heart rate variability or heart rate variation. In an example, a rate-responsive pacing mode can be used to adjust the patient risk profile.

20 Claims, 15 Drawing Sheets

(56) References Cited

U.S. PATENT DOCUMENTS

| | | | |
|---|---|---|---|
| 5,718,235 | A | 2/1998 | Golosarsky et al. |
| 5,891,176 | A * | 4/1999 | Bornzin .......................... 607/18 |
| 6,026,320 | A | 2/2000 | Carlson et al. |
| 6,694,188 | B1 | 2/2004 | Kroll |
| 6,907,287 | B1 | 6/2005 | Bevan et al. |
| 6,922,585 | B2 * | 7/2005 | Zhou et al. .................... 600/518 |
| 7,133,718 | B2 | 11/2006 | Bakken et al. |
| 7,142,920 | B2 | 11/2006 | Scheiner et al. |
| 2003/0144572 | A1 * | 7/2003 | Oschman et al. ............... 600/16 |
| 2004/0133247 | A1 * | 7/2004 | Stahmann et al. .............. 607/17 |
| 2004/0158292 | A1 | 8/2004 | Sheldon et al. |
| 2007/0016259 | A1 * | 1/2007 | Bakken et al. .................... 607/9 |
| 2008/0306564 | A1 * | 12/2008 | Wei et al. ........................ 607/18 |
| 2009/0299428 | A1 | 12/2009 | Chow |
| 2013/0150911 | A1 | 6/2013 | Perschbacher et al. |

OTHER PUBLICATIONS

"U.S. Appl. No. 13/707,186, Non Final Office Action mailed Sep. 20, 2013", 16 pgs.

"How Evolving Sensor Technology and Rate-Responsive Pacing Can Improve Clinical Outcomes in CI", [Online]. Retrieved from the Internet: <http://www.medscape.org/viewarticle/724645?src=emailthis>, (Jul. 19, 2010), 26 pgs.

"International Application Serial No. PCT/US2012/068251, International Search Report mailed Sep. 18, 2013", 5 pgs.

"International Application Serial No. PCT/US2012/068251, Invitation to Pay Additional Fees and Partial Search Report mailed May 24, 2013", 5 pgs.

"International Application Serial No. PCT/US2012/068251, Written Opinion mailed Sep. 18, 2013", 11 pgs.

"Normal ECG responses during and postexercise", [Online]. Retrieved from the Internet: <http://www.humankinetics.com/excerpts/excerpts/normal-ecg-responses-during-and-postexercise>, (Accessed Apr. 2, 2012), 2 pgs.

Dell'Orto, M.D., Simonetta, et al., "Sensors for rate responsive pacing", Indian Pacing and Electrophysiology Journal; 4(3), [Online]. Retrieved from the Internet: <http://www.ncbi.nlm.nih.gov/pmc/articles/PMC1501080/>, (2004), 137-145.

Fuenmayor, A. J, et al., "Heart rate and heart rate variability changes induced by right atrial pacing", International Journal of Cardiology, 54(1), (Apr. 19, 1996), 21-25.

Kilic, H., et al., "Heart rate turbulence and heart rate variability in patients with atrial synchronous ventricular pacing", Pacing Clin Electrophysiol., 31(9), (Sep. 2008), 1113-7.

Malik, Marek, "Heart rate variability: standards of measurement, physiological interpretation and clinical use. Task Force of the European Society of Cardiology and the North American Society of Pacing and Electrophysiology.", Circulation, 93(5), http://circ.ahajournals.org/cgi/content/full/93/5/1043, (Mar. 1, 1996), 1043-65.

"U.S. Appl. No. 13/707,186, Notice of Allowance mailed Jul. 21, 2014", 8 pgs.

"U.S. Appl. No. 13/707,186, Response filed Jul. 7, 2014 to Non Final Office Action mailed Apr. 8, 2014", 9 pgs.

"International Application Serial No. PCT/US2012/068251, International Preliminary Report on Patentability mailed Jun. 26, 2014", 13 pgs.

* cited by examiner

METHODS AND SYSTEMS FOR IDENTIFYING AND USING HEART RATE VARIABILITY AND HEART RATE VARIATION

CLAIM OF PRIORITY

This application claims the benefit of priority under 35 U.S.C. §119(e) of Perschbacher et al., U.S. Provisional Patent Application Ser. No. 61/569,350, entitled "HEART RATE DENSITY INDEX", filed on Dec. 12, 2011, and U.S. Provisional Patent Application Ser. No. 61/643,767, entitled "METHODS AND SYSTEMS FOR IDENTIFYING AND USING HEART RATE VARIABILITY AND HEART RATE VARIATION", filed on May 7, 2012, each of which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis by monitoring a patient condition. The devices can include one or more electrodes in communication with one or more sense amplifiers to monitor electrical cardiac activity within a patient, and can include one or more sensors to monitor one or more other internal patient parameters. Other examples of IMDs include implantable diagnostic devices, implantable drug delivery devices, or implantable neural stimulation devices.

Some IMDs detect events by monitoring electrical cardiac activity. In CFM devices, these events can include heart chamber expansions or contractions. By monitoring cardiac signals indicative of expansions or contractions, IMDs can detect abnormally slow heart rate, or bradycardia. In response to an abnormally slow heart rate, some CFM devices deliver electrical pacing stimulation energy to induce cardiac depolarization and contraction. The stimulation energy is delivered to provide a depolarization rate that improves hemodynamic function of the patient.

Normally, a patient's heart rate changes in response to a change in metabolic or physiologic need (e.g., during exercise). However, some patients' atrial depolarization rate may not adequately change in response to such changes. This condition is sometimes called chronotropic incompetence (CI). Examples of cardiac devices that can predict or recognize a chronotropically incompetent condition can be found in Scheiner et al., U.S. Pat. No. 7,142,920, entitled CHRONOTROPIC STATUS MONITOR FOR IMPLANTABLE MEDICAL DEVICE, which is hereby incorporated herein by reference in its entirety.

Pacemaker devices, such as dual-chamber devices, can use a rate-responsive pacing mode to treat patients with CI. In a rate-responsive, or rate-adaptive, pacing mode, information from a patient physical activity level sensor can be used by a pacemaker to adjust a patient heart rate. Some devices use more than one sensor to improve assessment of patient physical activity level, such as a quickly-reacting unspecific sensor (e.g., an accelerometer) and a more specific metabolic sensor (e.g., a respiration sensor).

In addition to CI, decreased heart rate variability can be associated with adverse cardiac outcomes including myocardial infarction or rapid progression of atherosclerosis and death from heart failure. Bakken et al., in U.S. Pat. No. 7,133,718, entitled METHOD AND APPARATUS FOR TEMPORARILY VARYING A PARAMETER IN AN IMPLANTABLE MEDICAL DEVICE, mention using a heart rate histogram to determine a heart rate profile. Bakken et al. also mention using the determined heart rate profile with a target rate profile to determine whether to use a rate variation feature of a pacemaker, such as an exercise simulator.

OVERVIEW

The present inventors have recognized, among other things, that a problem to be solved can include identifying patients at elevated risk of cardiac arrhythmia or death. The present subject matter can help provide a solution to this problem, such as by identifying or using a heart rate variability or heart rate variation to identify patients who can benefit from therapies that can reduce a risk of cardiac arrhythmia or death. In an example, a heart rate variability can include information about changes in intra-beat cardiac activity, or a heart rate variation can include information about changes in a patient heart rate, such as can be used to identify patients at elevated risk of arrhythmia and to identify patients with poor survival probabilities. Information about a heart rate variability or heart rate variation can be used to indicate a need for rate-responsive pacing. In some patients, rate-responsive pacing can be used to improve a patient survival probability.

Heart rate variability and heart rate variation can be determined using intrinsic cardiac activity information (e.g., information about natural sinus cardiac activity, such as a count of sinus heart beats), non-intrinsic cardiac activity information (e.g., information about augmented cardiac activity, such as a count of paced heart beats), or both intrinsic and non-intrinsic cardiac activity. Methods and systems to identify at-risk patients with sufficiently low heart rate variability or low heart rate variation are provided. A patient risk profile or a patient therapy can be adjusted, such as in response to an identified patient heart rate variability or heart rate variation.

In an example, a data input circuit can be configured to receive a cardiac activity signal of a patient. The cardiac activity signal can include information about intrinsic and non-intrinsic cardiac activity. A memory circuit can be configured to store information about the received cardiac activity signal. A processor circuit can be coupled to the memory circuit. The processor circuit can be configured to determine a heart rate variability using the stored information about the cardiac activity signal, including information about intrinsic and non-intrinsic cardiac activity. The processor circuit can be further configured to determine a rate-responsive pacing mode suitability indication for a patient using the determined heart rate variability.

In an example, a data input circuit can be configured to receive information indicative of a patient heart rate, such as including information about both intrinsic and non-intrinsic patient heart beats. A memory circuit can be configured to store information about the patient heart rate over time, such as in a heart rate histogram. A processor circuit, such as coupled to the memory circuit, can be configured to determine a heart rate variation using the stored information about the patient heart rate over time. The determined heart rate variation can be indicative of a number of both intrinsic and non-intrinsic patient heart beats within a specified heart rate range. The processor circuit can be further configured to compute a patient metric, such as using the determined heart rate variation.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Some cardiac function therapies can be provided using implantable or ambulatory medical devices such as pacemakers or defibrillators, among other devices. Some of these devices can be configured to provide electrostimulation to various body regions to effect a particular physiologic change. For example, a pacemaker device, a type of cardiac rhythm management device, can be configured to provide an electrostimulation to one or more areas of a heart, such as to initiate or augment a cardiac contraction.

A patient can receive a cardiac function therapy to address a cardiovascular disease or other dysfunction. Some cardiovascular or other diseases can cause a heart rate abnormality. For example, patients who suffer from chronotropic incompetence may be unable to effectively increase their heart rate in response to an increased metabolic need. Such patients can be treated using an implantable pacemaker with a rate-responsive pacing mode. An implantable pacemaker with a rate-responsive pacing mode can be configured to receive information about a patient's metabolic need, such as using one or more physiologic sensors coupled to the pacemaker and to the patient. For example, a physiologic sensor can include a physical activity level sensor, such as an accelerometer. A pacemaker with a rate-responsive pacing mode can use information from an accelerometer about metabolic need to automatically adjust a patient's heart rate.

Figure 1:
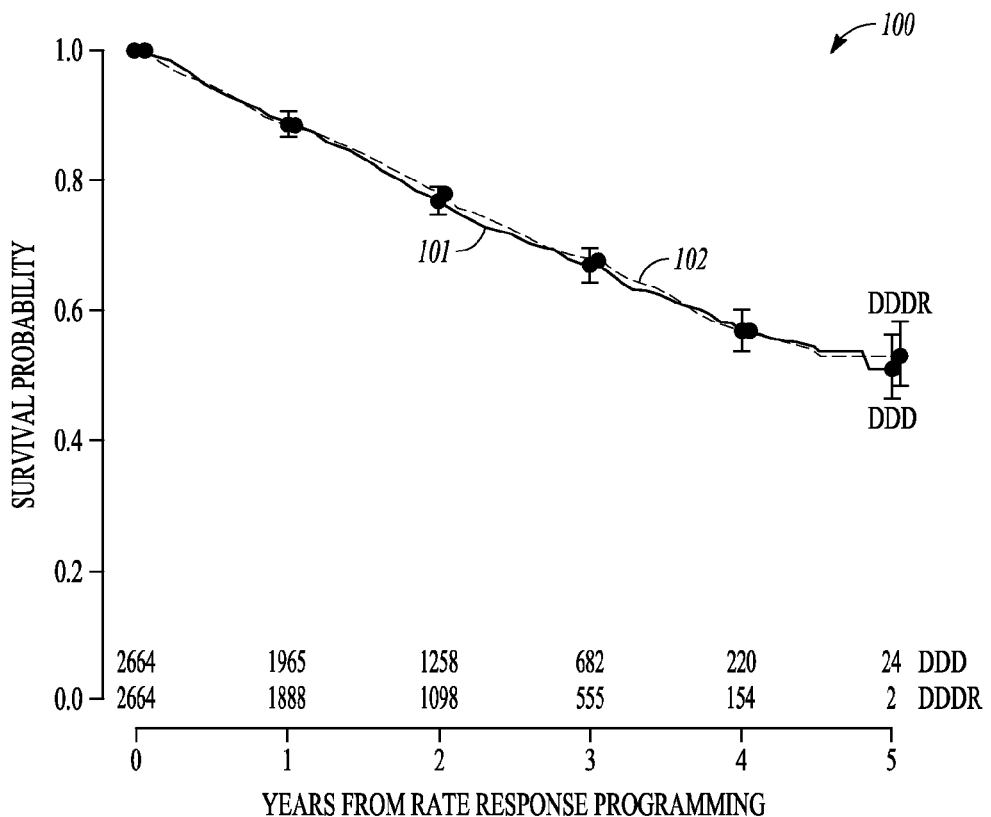
FIG. 1 illustrates generally an example of a patient survival probability over time.

FIG. 1 illustrates generally an example 100 of a survival probability for a particular population of 5328 patients. Half, or 2664, of the 5328 patients received pacing therapy from a pacemaker programmed to use a non-rate-responsive pacing mode, and the other half of the 5328 patients received pacing therapy from a pacemaker programmed to use a rate-responsive pacing mode. FIG. 1 includes a first survival probability trendline 101 corresponding to the patients using the non-rate-responsive pacing mode, and a second survival probability trendline 102 corresponding to the patients using the rate-responsive pacing mode. All of the patients had either a potentially lethal cardiac arrhythmia or had a left ventricular ejection fraction less than about 35%. All of the patients were indicated for a defibrillator.

In the example of FIG. 1, a significant difference is not observed between the survival probability of patients who received a rate-responsive pacing therapy and the survival probability of patients who did not receive a rate-responsive pacing therapy. As shown, at an initial time, a first group of 2664 patients received a non-rate-responsive pacing therapy (e.g., corresponding to the first survival probability trendline 101), and a second group of 2664 patients received a rate-responsive pacing therapy (e.g., corresponding to the second survival probability trendline 102). Each year following the initial time, about the same number of patients remained in each of the first and second populations. Thus, in this particular example, although some of the patients are believed to have benefitted qualitatively from rate-responsive pacing (e.g., as reported by improved quality of life indications), this benefit did not translate to a mortality or survival benefit over time. Patients in both groups were just as likely to die, according to this particular example.

The present inventors have recognized that including a rate-responsive pacing mode in a cardiac function management device can increase device size, complexity, and cost. The present inventors have further recognized that using a cardiac function management device with an enabled rate-responsive pacing mode can more quickly drain device resources, such as battery life, memory, or capacity to perform other functions. Accordingly, the present inventors have identified a solution to these problems and others, such as by identifying particular patients for whom survival probability can be improved using rate-responsive pacing. The patient populations can be identified, at least in part, using information about a heart rate variability or a heart rate variation.

A heart rate variability, or a heart rate variation, can include information about intrinsic (e.g., naturally occurring) and/or non-intrinsic (e.g., non-naturally occurring, e.g., at least partially electrostimulated) cardiac activity. A heart rate variability or heart rate variation can be determined using, among other techniques, an electrical or acoustic energy signal received from a patient. A heart rate variability can describe intra-beat heart rate changes, including a variability of a physiological parameter that can depend on heart rate. A heart rate variation can describe changes in heart rate over multiple cardiac cycles.

An intra-beat heart rate variability can include information about a cardiac characteristic or variable that can change with heart rate, such as a QT interval, a septal Q-wave amplitude, an ST segment slope, a T-wave morphology, or a P-wave amplitude or morphology, among others. An intra-beat heart rate variability can include information about a relationship between one or more intra-beat variables. Multiple time- and frequency-domain methods can be used to determine heart rate variability in spontaneous, intrinsic beats, such as described by Malik et al., in HEART RATE VARIABILITY: STANDARDS OF MEASUREMENT, PHYSIOLOGICAL INTERPRETATION, AND CLINICAL USE, Circulation, vol. 93, p. 1043-1065 (1996), which is hereby incorporated herein by reference in its entirety.

Heart rate variability or heart rate variation can include patient heart rate changes over periods that exceed a single heart beat, or that exceed an interval between adjacent heart beats. For example, a heart rate variation can include information about multiple cardiac cycle lengths, such as can be determined using information about a series of R-R intervals. A heart rate variability or heart rate variation can include information about a frequency of a particular type of electric or acoustic event (e.g., an R-wave peak, a threshold crossing of an electrical signal magnitude, an S1 event, etc.), such as over a specified period. A heart rate variability or heart rate variation can describe oscillations or other changes among multiple cardiac cycles, such as for intrinsic and/or non-intrinsic cardiac activity. Information about a patient heart rate can be determined using information about a patient heart rate variability or a patient heart rate variation.

A patient heart rate can be determined, such as using information about intrinsic and/or non-intrinsic cardiac activity (e.g., including sinus and/or paced heart beats). For example, a patient heart rate can be determined using a patient electric or acoustic energy signal, such as using a series of R-wave peaks in a QRS waveform from a patient ECG, or by using acoustic heart sound timing information. Heart rate fluctuations, or heart rate variation, can be analyzed and used to indicate a patient health status, or to indicate a need for a patient therapy, such as a rate-responsive pacing therapy. A heart rate variation can include information about a number, or count, of intrinsic or non-intrinsic heart beats, such as corresponding to a specified heart rate range.

Figure 2:
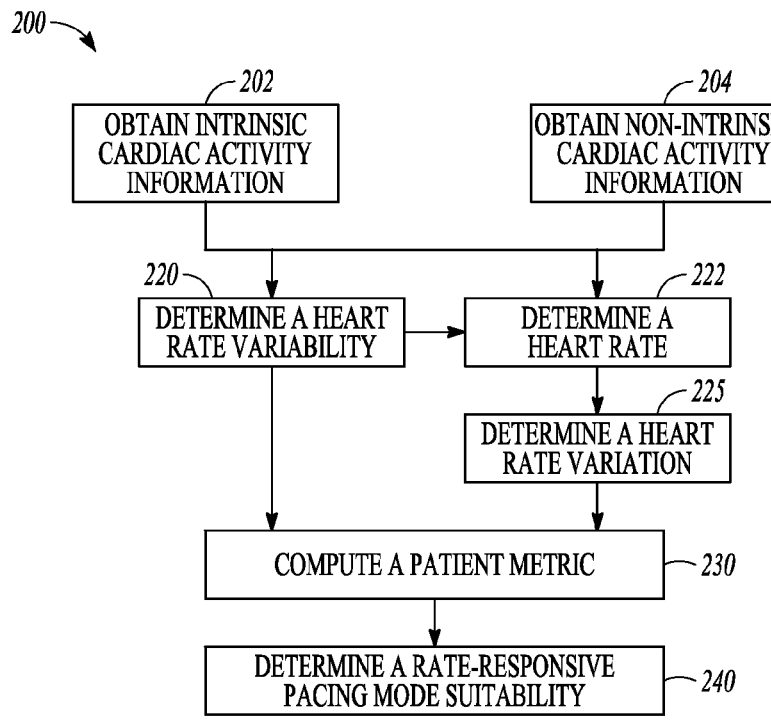
FIG. 2 illustrates generally an example that can include computing a patient metric or determining a rate-responsive pacing mode suitability.

Information about a heart rate variability or a heart rate variation can be used to compute a patient metric or to determine a patient therapy. FIG. 2 illustrates generally an example 200 that can include determining a heart rate variability or determining a heart rate variation.

At 202, intrinsic cardiac activity information can be obtained. Intrinsic cardiac activity information can include information about natural cardiac activity, such as information about spontaneous activation of nodal tissue, or electric or acoustic information about natural cardiac mechanical activity. The obtained intrinsic cardiac activity information can include information about one or more intrinsic heart beats, such as a beat count.

At 204, non-intrinsic cardiac activity information can be obtained. Non-intrinsic cardiac activity information can include information about non-natural cardiac activity, such as information about paced or otherwise augmented cardiac activity. The non-intrinsic cardiac activity information can include information about one or more non-intrinsic heart beats (e.g., paced heart beats or paced portions of heart beats), such as a beat count. The non-intrinsic cardiac activity information can include information from a medical device about a cardiac therapy, such as timing information or information about a characteristic of the cardiac therapy. The information about intrinsic or non-intrinsic cardiac activity can include information about all or a portion of a cardiac cycle, such as including information about one or more of atrial, ventricular, or other venous or neural activity.

At 220, a heart rate variability can be determined using the information about intrinsic and/or non-intrinsic cardiac activity. For example, the heart rate variability determined at 220 can be determined using information about an intra-beat variable (e.g., a QT interval, a P-wave amplitude, etc.), such as a variable indicative of a patient heart rate. An implanted device such as a pacemaker can be used to sense intrinsic cardiac activity (e.g., at 202), or provide information about non-intrinsic cardiac activity (e.g., at 204). The implanted pacemaker can include a memory circuit that can be used to record the cardiac activity information, such as including timing information (e.g., R-R interval information) corresponding to the intrinsic and non-intrinsic cardiac activity.

At 220, the determined heart rate variability can provide an indication about patient heart rate changes, such as whether the patient's heart rate is relatively static (e.g., corresponding to a low variability) or dynamic (e.g., corresponding to a high variability). A static heart rate can be a rate that is constant or nearly constant, such as due to a cardiac dysfunction or a sedentary lifestyle, among other factors. A static heart rate can correspond to a poor patient survival probability. A dynamic heart rate, on the other hand, can be a rate that is not constant, such as a heart rate that sufficiently responds to changes in metabolic demand. A dynamic heart rate can fluctuate according to a normal patient's sleep/wake cycles or other activities. A dynamic heart rate can correspond to an improved patient survival probability.

At 222, the intrinsic and/or non-intrinsic cardiac activity information (e.g., obtained at 202 and 204) can be used to determine a heart rate. For example, the intrinsic and non-intrinsic cardiac activity information can include information about an interval between cardiac depolarizations that can be used to determine a patient heart rate. At 222, a heart rate variability (e.g., determined at 220) can be used to determine the heart rate, such as using one or more variables indicative of a heart rate (e.g., QT interval, Q-wave amplitude, etc.).

At 225, a heart rate variation can be determined using the heart rate. Determining a heart rate variation at 225 can include determining an amount of heart rate change, such as over a specified period. For example, a heart rate variation can indicate how often a patient experiences a particular heart rate range (e.g., 60 to 65 beats per minute) over a specified period, such as a 24 hour period. A low heart rate variation can correspond to poor patient outcomes, and high heart rate variation can correspond to improved patient survival probability.

As described above, obtaining the intrinsic and non-intrinsic cardiac activity information (e.g., at 202 and 204) can include obtaining a signal indicative of cardiac mechanical or electrical activity. For example, a maximum, a minimum, a slope, or a characteristic, such as a morphology characteristic, of a cardiac activity signal can be used to determine the heart rate variability at 220, or to determine the heart rate variation at 225. A frequency of a cardiac activity signal can correspond to the intrinsic or non-intrinsic cardiac activity information. For example, a signal indicative of cardiac electrical activity can include a frequency component indicative of a patient heart rate. The frequency component can be used to determine a distribution of the patient heart rate information (e.g., to determine a heart rate variation at 225), such as by monitoring changes in the frequency component over time.

At 230, the determined heart rate variability or heart rate variation can be used to compute a patient metric. The patient metric computed at 230 can include, among others, a patient health status, a patient risk profile, a patient therapy indication, or a patient survival probability, such as described in further detail herein.

At 240, the patient metric can be used to determine a rate-responsive pacing mode suitability. The patient metric computed at 230 can include a heart rate variation metric or a heart rate variability metric. The heart rate metric(s) can be compared to a corresponding baseline or threshold metric, such as to determine whether a particular therapy (e.g., a rate-responsive pacing therapy) is recommended. For example, when the determined heart rate variability is low compared to the baseline (e.g., corresponding to a relatively static heart rate), a rate-responsive pacing therapy can be indicated. When the determined heart rate variability is high compared to the baseline (e.g., corresponding to a relatively dynamic heart rate), a rate-responsive pacing therapy can be contraindicated. When a patient with low heart rate variability receives a rate-responsive pacing therapy, the patient's survival probability can be improved.

Patient heart rate information, such as obtained from intrinsic or non-intrinsic cardiac activity information, can be stored in a heart rate histogram. The heart rate histogram can include one or more histogram bins that correspond to specified heart rates, heart rate ranges, or heart rate variability variable ranges.

A heart rate variation histogram can include multiple bins corresponding to different ranges of heart rates. A first histogram bin can be centered at a particular heart rate n. The heart rate can be expressed in terms of beats per minute (bpm), or in terms of an interval (e.g., corresponding to an R-R interval, such as in milliseconds). A heart rate $n_b$ can be a number of occurrences per unit time (e.g., bpm), or a heart rate $n_s$ can correspond to a particular heart rate interval duration (e.g., R-R interval, such as in milliseconds). Each histogram bin can have a corresponding width, such as can be expressed in terms of a number of a beats or an interval. For example, a histogram bin can have a width of $m_b$ beats or $m_s$ milliseconds.

In a heart rate variation histogram with bins corresponding to ranges of bpm, a number of detected heart beats (e.g., intrinsic and/or non-intrinsic beats) can be counted and recorded in a first histogram bin, such as a bin centered at $n_b$ and having a width $m_b$. The first bin can be bound by a first heart rate $n_b-(m_b/2)$ and a second heart rate $n_b+(m_b/2)$. For example, where $n_b$ is 60 beats per minute (bpm), and $m_b$ is 10 beats, the number of intrinsic and non-intrinsic heart beats between 55 and 64 beats can be counted and recorded in the histogram bin. A second histogram bin can be adjacent to the first, and can be centered at $n_b+m_b$. The second histogram bin can have a width of $m_b$ beats, or it can be wider or narrower. Additional histogram bins can be provided to record the heart beat information. A heart rate histogram can include histogram bins of different or various widths, such as can be fixed or variable.

Figure 3A:
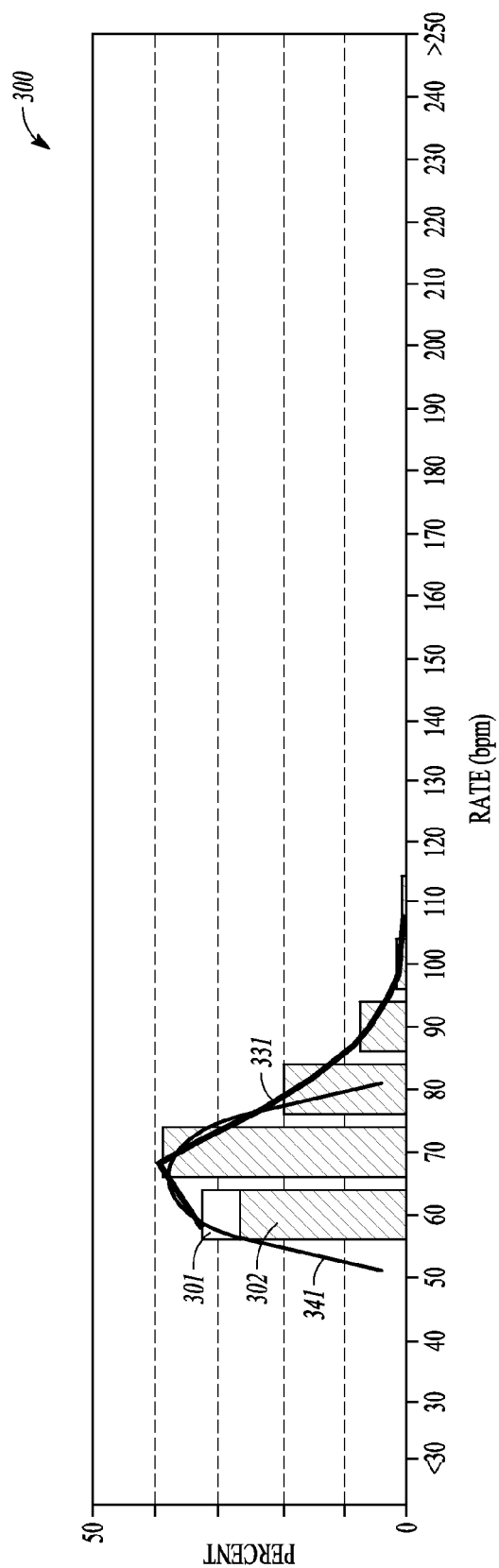
FIG. 3A illustrates generally an example that can include a heart rate variation histogram.

A heart rate variability or a heart rate variation can be determined using a heart rate histogram. FIG. 3A illustrates generally a graphical example of a heart rate variation histogram 300. The heart rate variation histogram 300 includes a series of adjacent, fixed-width, 10-beat histogram bins. In the example of FIG. 3A, the histogram 300 can include information about non-intrinsic beats 301 and information about intrinsic beats 302, such as for one or more patients. A histogram bin can include information about both non-intrinsic beats and intrinsic beats, such as when non-intrinsic and intrinsic beats occur at similar rates. A relationship between the number of non-intrinsic beats and the number of intrinsic beats, or between the number of non-intrinsic beats and the total number of intrinsic and non-intrinsic beats, can be determined. For example, as shown in the example of FIG. 3A, about 6% of the total beats illustrated in the heart rate histogram 300 are paced beats.

In the example of FIG. 3A, the heart rate variation histogram 300 can include populated histogram bins centered at 60, 70, 80, 90, 100, and 110 bpm. The histogram bin centered at 60 bpm can include about 33% of the total number of beats recorded (e.g., including intrinsic and non-intrinsic beats). The bins centered at 70, 80, 90, 100, and 110, can include, respectively, about 38%, 20%, 6%, 2%, and 1%, of the total number of beats recorded. A bin 321, centered at 70 bpm, can be the most-populated bin of the histogram 300 because the heart beat count corresponding to the bin 321 includes the most number of beats.

A heart rate variation can be determined using all or a portion of a heart rate variation histogram. For example, in a heart rate variation histogram, a most-populated histogram bin can be identified. That is, in a histogram where each histogram bin corresponds to a particular heart rate range and includes a count of heart beats in that range, the histogram bin or bins corresponding to the greatest count of heart beats can be identified. A size, or population, of the most-populated histogram bin(s) can be compared, such as to an overall population, or to an overall distribution of the histogram bins. Information about a relationship between the most-populated histogram bin(s) and the other bins can be used to determine a heart rate variation.

A heart rate variation can be determined (see, e.g., FIG. 2 at 225) using an index of a heart rate variation histogram. For example, an index, such as a variation index, of the variation histogram 300 can include information about the most-populated histogram bin 321. An index of the variation histogram 300 can include information about the population of the bin 321 relative to the total number of beats recorded. For example, the variation index of the heart rate variation histogram 300 can be 0.38, or 38%.

A heart rate variation can be determined in other ways, such as using a characteristic of a heart rate variation histogram. A histogram characteristic can include a morphology characteristic, such as a characteristic that describes a size or shape of the heart rate histogram. A morphology characteristic can include an indication of a relative size or shape of one or more specified histogram bins. For example, a morphology characteristic can include an area of one or more histogram bins. A morphology characteristic can include a characteristic of a histograph, or frequency polygon, such as can be formed by joining points of the histogram with one or more line segments (e.g., by joining the tops of the histogram bins). A morphology characteristic can include a characteristic of a function corresponding to the histograph or frequency polygon.

In the example of FIG. 3A, the heart rate variation histogram 300 can include a variation histograph 331. A characteristic of the variation histograph 331, such as a maximum, minimum, or area under the curve, among other characteristics, can be used to determine a heart rate variation.

A function can correspond to a population of one or more of the histogram bins. For example, the heart rate variation histogram 300 can include a variation function 341 that can correspond to the populations of one or more bins. The variation function 341 can be a function of the populations of the three most-populated histogram bins (e.g., the histogram bins centered at 60, 70, and 80 bpm). For example, the function 341 can be a parabolic function of the form $y=-0.12x^2+15.45x-480$. A characteristic of the function 341, such as a coefficient, maximum, minimum, integral, derivative, or inflection point, among other characteristics, can be used to determine the heart rate variation.

More than one histogram bin in a heart rate variation histogram can be used to determine a heart rate variation. For example, a heart rate variation can be determined using a combination of bins, such as using an average of populations in the k most-populated bins. In an example, a standard deviation of all heart beats in all or a portion of the histogram can be used to determine a heart rate variation.

A characteristic of a variation histogram can be used or adjusted to determine a heart rate variation. A peak histogram bin can be used, as described above, and the peak bin can be compared to the next k largest bins, such as to determine whether there is a significant difference (e.g., greater than a specified threshold difference) in the bin populations. When adjacent or near-by bins are found to have similar populations, one or more bin widths or bin centers can be adjusted. For example, where a 10-beat bin, such as centered at 60 bpm, includes 90 beats, and an adjacent 10-beat bin, such as centered at 70 bpm, includes 100 beats, an adaptive algorithm can be used to determine whether a 10-beat (or other sized) bin centered at 65, for example, would include more than 100 beats. After the histogram is optimized, such as by adjusting a bin center or bin width, the heart rate variation or heart rate variability can be determined (e.g., at 220 or 225).

A characteristic of a variation histogram can be monitored or trended over time. For example, a variation histogram can correspond to a particular time interval or number of beats. The particular time interval or number of beats can be determined using a characteristic derived from the histogram, such as using an indication of histogram characteristic stability. For example, when a particular histogram characteristic changes by more than a specified amount, a new histogram can be collected and optionally compared to a previous histogram. Histogram changes can be identified and correlated with clinical events, behavioral events, or therapeutic interventions, among other causes.

Other heart rate variations or variation indices can be determined using a heart rate variation histogram. For example, a heart rate variation can be determined for different categories of heart beats, such as for each of intrinsic and non-intrinsic beats. In an example, a heart rate variation histogram can be determined using only non-intrinsic heart beats. A heart rate variation corresponding to the non-intrinsic beats can include a number of non-intrinsic beats in a bin having a greatest number of beats in the variation histogram. Information about non-intrinsic heart beats can be included in a heart rate variation histogram for a cardiac interval that begins with a non-intrinsic beat, for a cardiac interval that ends with a non-intrinsic beat, or for a cardiac interval that begins and ends with a non-intrinsic beat.

Portions of a heart rate histogram can be adjusted or excluded, such as before determining a heart rate variation. For example, when patient heart rate information includes information from a patient with a pacemaker that uses a lower rate limit to regulate heart rate, a heart rate variation can be determined after discarding all beats at or below the lower rate limit. Arrhythmic beats can be excluded. Rapid beats that occur more quickly than a specified threshold rate can be excluded, such as beats in the range of atrial fibrillation or frequent ectopic beats. Beats above a specified age-related maximum heart rate can be excluded. Beats during periods of physical activity, during one of daytime or nighttime, or during known drug regimens, can be excluded, modified, or singled out for analysis. Portions of a histogram that have a non-Gaussian distribution can be excluded from heart rate variation analyses.

One or more histogram bins can be weighted to determine a heart rate variation. For example, a specified histogram bin(s) corresponding to a specified heart rate, or range of heart rates, can be weighted. For example, a histogram bin that includes heart beat information for 70-79 bpm can be weighted more heavily than a histogram bin that includes heart beat information for 40-49 bpm. Weighting a histogram bin can include adjusting a histogram index or adjusting a characteristic of a histogram.

Although a histogram is a convenient mechanism to visually represent heart rate information, it is not necessary to generate a histogram to provide a heart rate variation or heart rate variability. For example, heart rate information can be derived from a continuous signal. Timing or frequency components of the continuous signal can be analyzed to determine the heart rate variation or heart rate variability. For example, a cardiac activity signal can have a frequency that corresponds to a patient heart rate. Frequency changes of the signal, such as together with timing information about the frequency changes, can be used to provide information about how long or how often a patient experiences a particular heart rate. For example, a particular cardiac activity signal can have a first frequency $f_1$, such as corresponding to a first heart rate, such as corresponding to a duration $t_1$, and a second frequency $f_2$, such as corresponding to a second elevated heart rate, such as corresponding to a duration $t_2$. An index of the frequency information can include a ratio of the durations $t_1$ and $t_2$. The index can be used to provide the heart rate variation or heart rate variability.

Figure 3B:
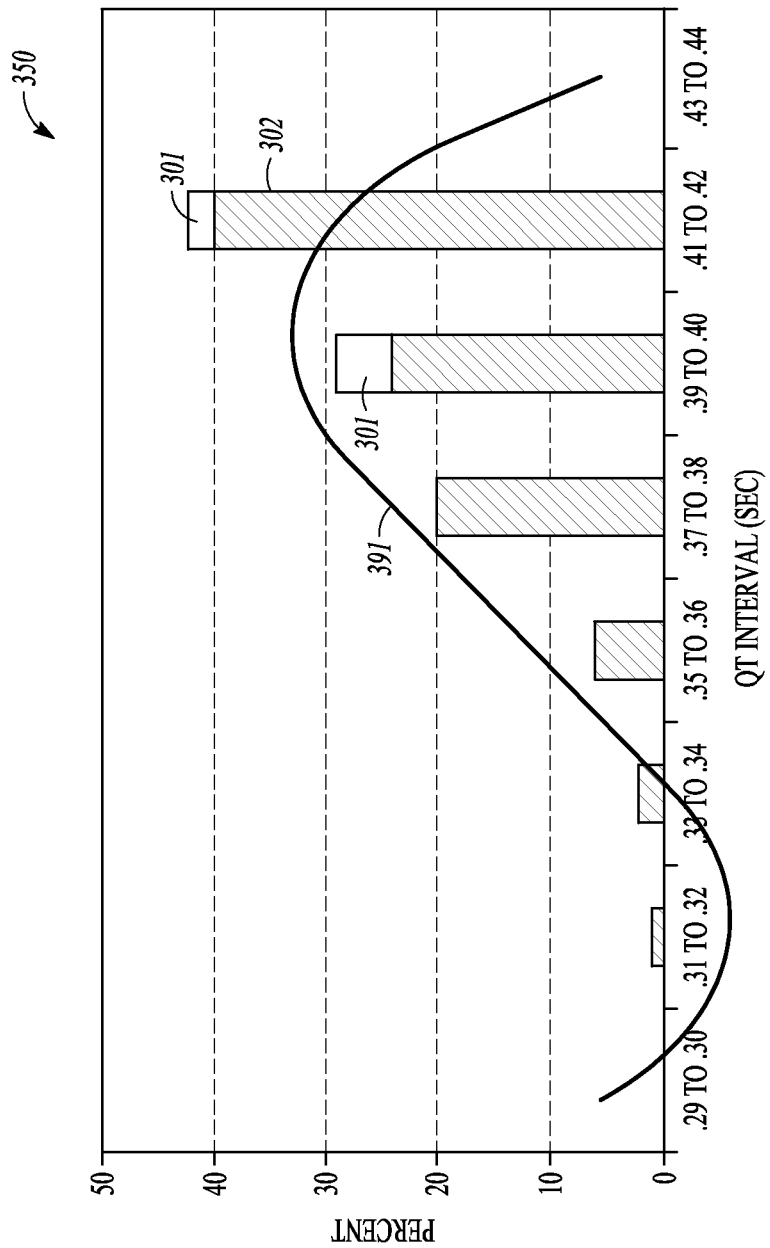
FIG. 3B illustrates generally an example that can include a heart rate variability histogram.

The example of FIG. 3A is a heart rate variation histogram 300 in which the histogram bins represent ranges of heart rates. In an example, a heart rate variability histogram can include histogram bins that represent a heart rate variability variable. FIG. 3B illustrates generally an example of a heart rate variability histogram 350 in which the histogram bins represent ranges of QT intervals (e.g., an intra-beat variable). The histogram 350 can include information about the non-intrinsic beats 301 and information about the intrinsic beats 302. The histograms 300 and 350 can illustrate the same underlying cardiac activity information expressed in different ways.

A heart rate variability can be determined using all or a portion of a heart rate variability histogram. For example, similarly to the determination of the heart rate variation described above in the example of FIG. 3A, a most-populated histogram bin in a heart rate variability histogram can be identified and used to provide information about a heart rate variability. A size or population of a histogram bin (e.g., a most-populated histogram bin) can be compared, such as to an overall population, or to an overall distribution of the variability histogram bins, to determine the heart rate variability. In an example, a heart rate variability index of a heart rate variability histogram can be used, such as described above in the example of FIG. 3A for the heart rate variation index. As illustrated in the example of FIG. 3B, the variability index can be 0.42, or 42%, such as corresponding to the most-populated bin of the heart rate variability histogram 350.

A heart rate variability can be determined using a characteristic of a heart rate variability histogram, such as a morphology characteristic, such as including a shape or area of a portion of the histogram. Bin widths, locations, weights, or other characteristics of the bins in a heart rate variability histogram can be adjusted, such as described above in the example of FIG. 3A. A heart rate variability can be determined using a histogram or frequency polygon corresponding to a heart rate variability histogram, such as described herein.

A function can correspond to a population of one or more of the variability histogram bins. For example, the heart rate variability histogram 350 can include a variability function 391 that can correspond to the populations of all of the bins (or a subset of the bins). The variability function 391 is a third degree polynomial function of the form $y=-1.10x^3+13.80x^2-43.49x+34.86$. A characteristic of the variability function 391, such as a coefficient, maximum, minimum, integral, derivative, or inflection point, among other characteristics, can be used to determine the heart rate variability. For an illustrative example, where a maximum of the variability function 391 is used as a variability index, the heart rate variability index corresponding to the heart rate variability histogram 350 can be about 0.33 or 33%.

A patient metric can be computed (e.g., at 230 in the example of FIG. 2) using one or more of a heart rate variability, variability index, heart rate variation, or variation index. A patient health status metric, for example, can be determined using one or more of the indices. One or more thresholds can correspond to the indices. A first variability threshold can be used to indicate a particular patient health status, and a first variation threshold can be used to indicate the same or a different patient health status. A common threshold can be used with both a variation index and a variability index to provide information about a patient health status.

Figure 4:
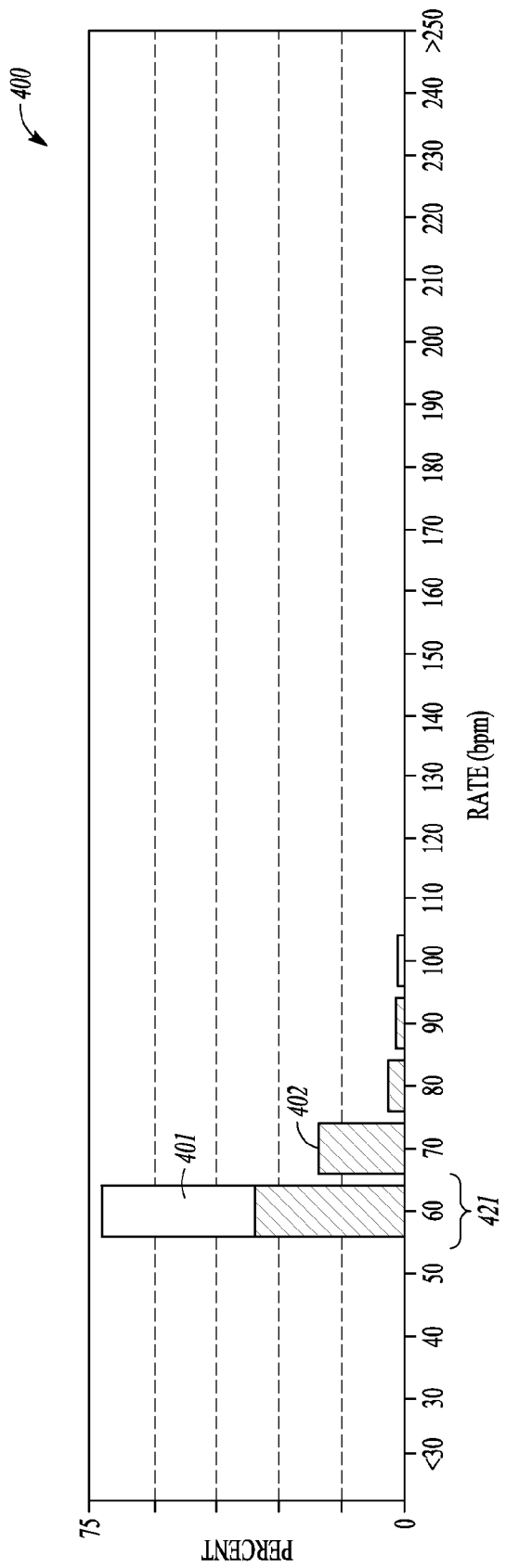
FIG. 4 illustrates generally an example that can include a heart rate variation histogram.

FIG. 4 illustrates generally an example of a heart rate variation histogram 400. The heart rate variation histogram 400 includes a series of adjacent, fixed-width, 10-beat histogram bins that are populated using information about non-intrinsic beats 401 and information about intrinsic beats 402. In the illustrative example of FIG. 4, about 32% of the total beats in the histogram 400 are non-intrinsic beats 401.

In the example of FIG. 4, the heart rate variation histogram 400 can include, among others, histogram bins centered at 60, 70, 80, 90, and 100 bpm. The histogram bin centered at 60 bpm can include about 73% of the total number of beats recorded (e.g., including sensed and/or paced beats). The bins centered at 70, 80, 90, and 100, can include, respectively, about 20%, 5%, 1%, and 1%, of the total number of beats recorded. The bin centered at 60 bpm can include the greatest number of beats (73%) of any bin in the heart rate variation histogram 400. In an illustrative example, an index of the histogram 400 can be about 0.73, or 73%, such as corresponding to the most-populated bin 421.

A high variation index (e.g., greater than a threshold variation index, such as greater than about 0.7) can correspond to a heart rate that is substantially static, or constant. Thus, a high variation index can correspond to low heart rate variation. The heart rate variation histogram 400 illustrates a low heart rate variation because most of the heart beats (e.g., about 73%) occur within a particular 10-beat window. A low variation index (e.g., less than about 0.7) can correspond to a high heart rate variation because the low variation index corresponds to a heart rate that is dynamic, or changing over time. For example, the heart rate variation histogram 300 illustrates high heart rate variation because no particular 10-beat window corresponds to more than a threshold percentage (e.g., 70%) of the total beats. An index threshold for determining a high or low variation or variability index (e.g., 0.7) can be adjusted, such as according to the number of beats per window. For example, as the size of the window is decreased (e.g., from 10-beats to 5-beats), the index threshold can be correspondingly reduced.

Figure 5:
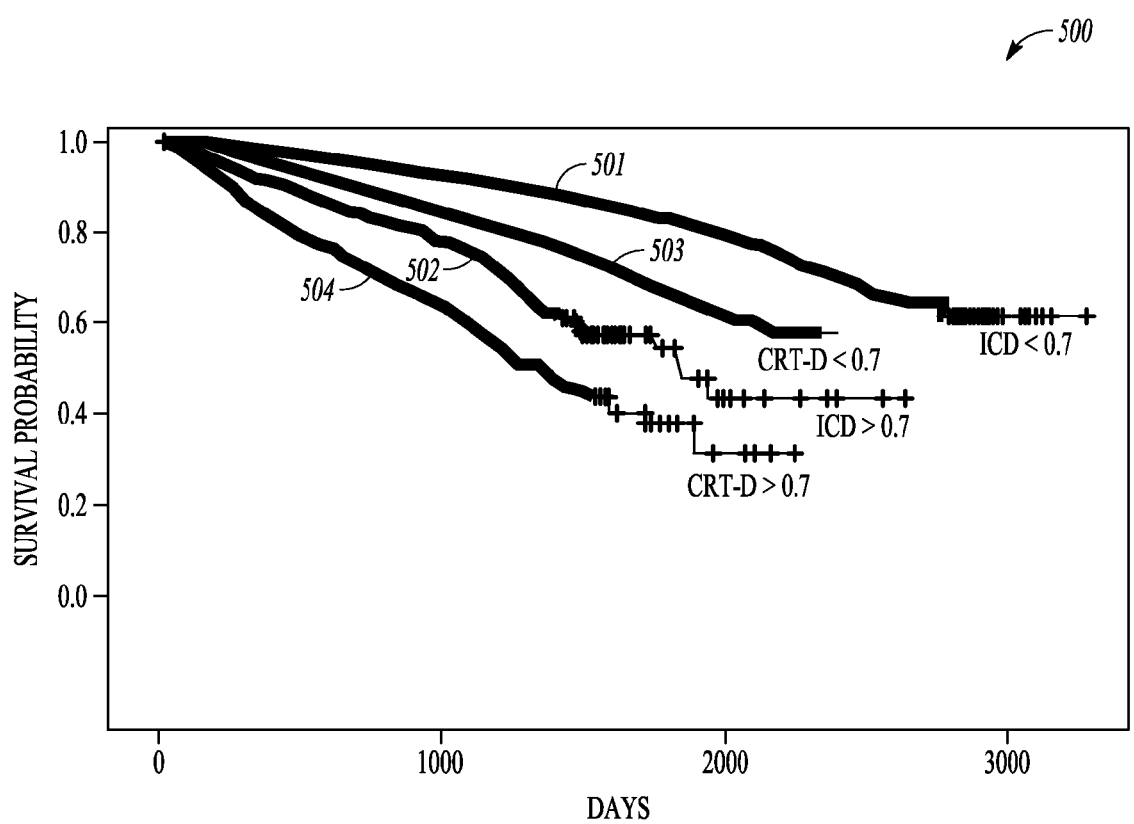
FIG. 5 illustrates generally an example that can include patient survival probability trends corresponding to different patient populations.

Information about heart rate variation or heart rate variability can indicate a patient survival probability. For example, FIG. 5 illustrates generally a chart 500 that includes information about patient survival rate over time for particular groups of patients with different heart rate variation indices and who were treated with different types of cardiac function management devices. The chart 500 includes information from devices implanted in actual patients. The chart 500 includes first and second patient mortality curves 501 and 502 that correspond to patients treated with implantable cardioverter/defibrillator devices (ICDs), and third and fourth patient mortality curves 503 and 504 that correspond to patients treated with cardiac resynchronization and defibrillation devices (CRT-Ds).

The first and third patient mortality curves 501 and 503 correspond to patients who have a heart rate variation index of less than about 0.7. The second and forth patient mortality curves 502 and 504 correspond to patients who have a heart rate variation index of greater than about 0.7. The heart rate variation, or variation index (or, e.g., heart rate variability, or variability index), can be determined according to the discussion of FIG. 2, 3A, 3B, or 4, herein. As shown in the example of FIG. 5, some patients who have a particular heart rate variability index and/or a particular device can be more likely to survive than others.

In FIG. 5, the first and third patient mortality curves 501 and 503 correspond to particular patients whose heart rate variation index is less than about 0.7. A survival probability for these patients can be greater than a survival probability for patients whose heart rate variation index is greater than about 0.7. Accordingly, patients with a more dynamic heart rate (e.g., patients who have a heart rate variation index less than about 0.7) can be more likely to survive than patients with a less dynamic heart rate (e.g., patients who have a heart rate variation index of greater than about 0.7). Thus, as illustrated in the example of FIG. 5, a heart rate variation index can be an indication of patient survival probability for some groups of patients.

Figure 6:
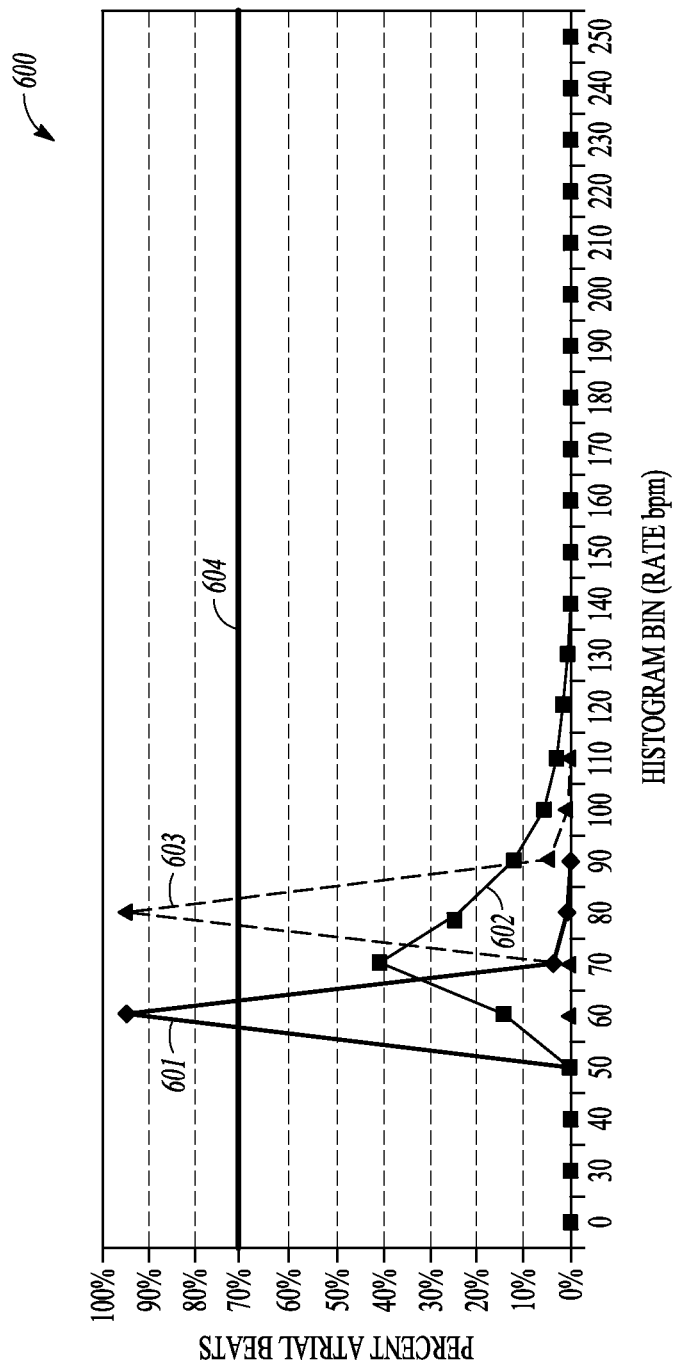
FIG. 6 illustrates generally an example that can include a heart rate histograph corresponding to three patients.

FIG. 6 illustrates generally an example 600 that can include histograph information corresponding to several actual patients. The example 600 illustrates a relative percentage of atrial beats (e.g., heart beats) that correspond to a particular range of heart rates (e.g., a 10-beat histogram bin). The example 600 includes a first histograph 601 corresponding to a first patient, a second histogram 602 corresponding to a second patient, and a third histograph 603 corresponding to a third patient. The example 600 further includes a heart rate variation threshold index 604. In the example of FIG. 6, the first histogram 601 can correspond to a heart rate variation index of about 0.95. The third histogram 603 can correspond to a heart rate variation index of about 0.94. Accordingly, because the first and third histographs 601 and 603 correspond to elevated heart rate variation indices (e.g., heart rate variability indices that exceed the threshold index 604), the first and third patients can have a reduced survival probability (see, e.g., FIG. 5 showing that an elevated heart rate variation index can correspond to reduced survival probability). In the example of FIG. 6, the second histogram 602 can correspond to a heart rate variation index of about 0.4. Because the second histograph 602 corresponds to a heart rate variation index that does not exceed the threshold index 604, the second patient can have a better survival probability than the first and third patients.

Heart rate variability information can be used to provide a suitability indication for a therapy, such as a rate-responsive pacing therapy. In the example of FIG. 6, the first patient, corresponding to the first histograph 501, can have a low heart rate variation, or a high heart rate variation index. However, the first patient's heart rate can be concentrated at a low heart rate (e.g., at about 60 bpm). Because the first patient's heart rate is concentrated at the low heart rate, the first patient's survival probability can be improved using a rate-responsive pacing mode to change the first patient's heart rate variation index. The rate-responsive pacing mode can be used to vary the first patient's heart rate and decrease the patient's heart rate variation index. If the first patient's heart rate variation index can be sufficiently decreased (e.g., below the threshold index 604), then the first patient's survival probability can be improved (see, e.g., FIG. 5, explaining that heart rate variation can be an indication of patient survival probability).

In the example of FIG. 6, the second patient, corresponding to the second histograph 602, has a relatively nominal heart rate variation and variation index. Because the second patient has a relatively healthy, or dynamic, heart rate, a pacing mode change can be contraindicated. For example, if the second patient does not have a rate-responsive pacing mode enabled, the second patient's nominal heart rate variation index suggests that the patient's survival probability will not be improved by enabling a rate-responsive pacing mode. If the second patient already has a rate-responsive pacing mode enabled, the relatively nominal heart rate variation index can be confirmation that the rate-responsive pacing mode is properly adjusting the second patient's heart rate and improving the patient's survival probability.

In the example of FIG. 6, the third patient, corresponding to the third histograph 603, can have a low heart rate variation or a high variation index. Because the third patient's heart rate is concentrated at a relatively high heart rate (e.g., at about 80 bpm), enabling a rate-responsive pacing mode may not be effective to reduce the patient's heart rate variation index or to reduce the patient's risk of death. If the third patient already has a rate-responsive pacing mode enabled, adjusting a pacing parameter, such as the lower rate limit (e.g., to a lesser limit), may help to reduce the patient's heart rate variation index.

Figure 7:
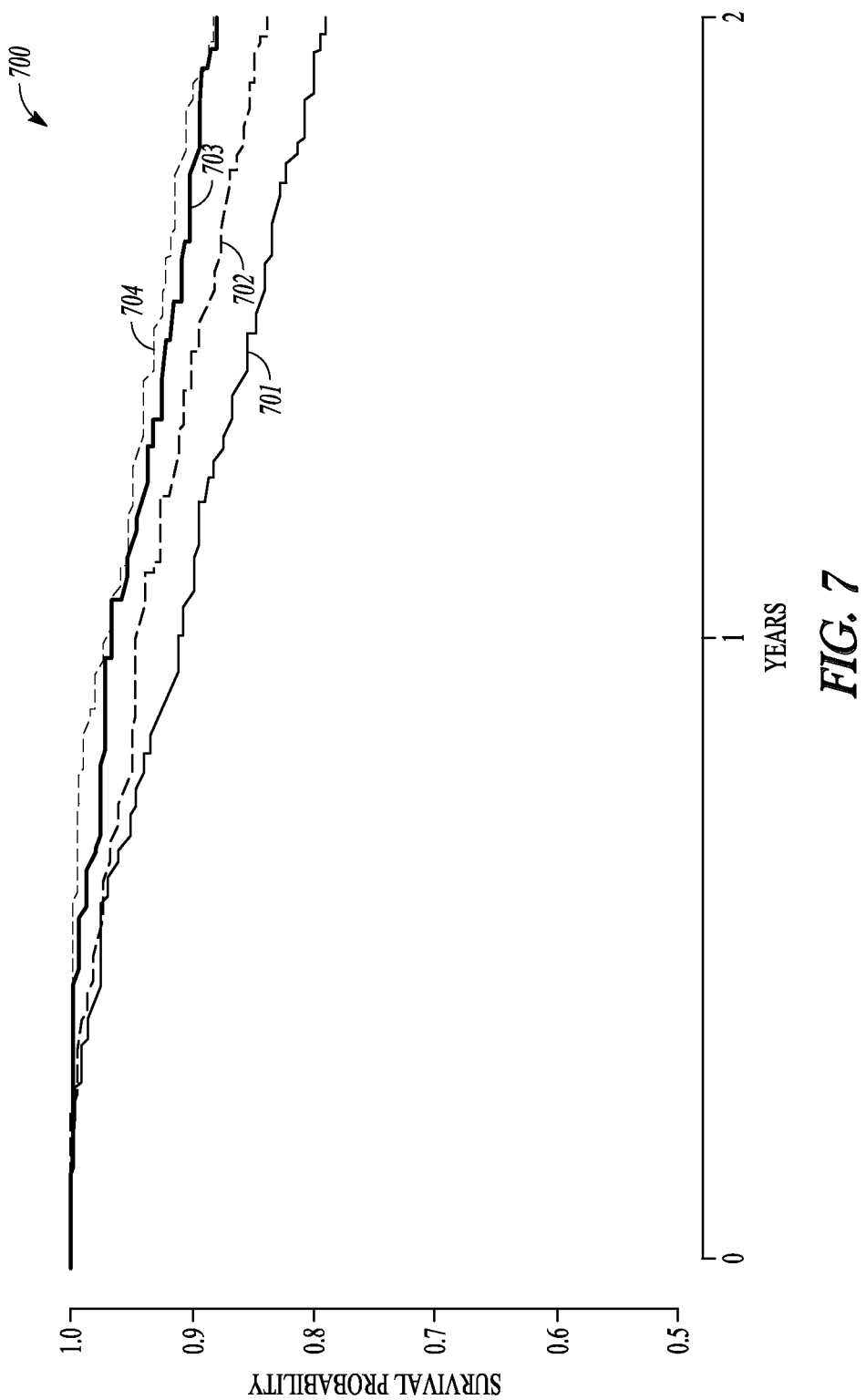
FIG. 7 illustrates generally an example that can include patient survival probability trends corresponding to different patient populations.

FIG. 7 illustrates generally an example 700 of a study that shows rate-responsive pacing can be used to influence patient survival probability. The example 700 includes patient data for particular populations of matched patients. The matched patients share similar characteristics, such as sex, device-type, device operating mode, patient age, or time since device implant, among other characteristics.

In the example of FIG. 7, all of the patients were matched at the beginning of the study, and all of the patients had previously-implanted pacemaker devices that initially operated in a non-rate-responsive, dual chamber pacing mode (e.g., in a "DDD pacing mode"). All of the patients received pacing (e.g., atrial pacing) at least 30% of the time. During the course of the study, a portion of the patients had pacemaker devices that were re-programmed to enable a rate-responsive pacing mode (e.g., a "DDDR pacing mode").

In the example of FIG. 7, first and second survival probability curves 701 and 702 correspond to first and second populations that were initially matched. In the example of FIG. 7, the first population remained in a non-rate-responsive pacing mode throughout the study. In addition, the first population had a heart rate variation index that exceeded a heart rate variation threshold index (e.g., the heart rate variation index for each patient in the first population was greater than about 0.7). That is, patients in the first population had relatively constant heart rates.

A survival probability of the particular patients in the first population can be improved, such as by re-programming the patients to a rate-responsive pacing mode. FIG. 7 illustrates this improvement using the second survival probability curve 702. As described above, the second survival probability curve 702 corresponds to the second population that was initially matched to the first population. At the beginning of the study, the first population and the second population had relatively constant heart rates (e.g., the first and second populations had patients with heart rate variation indices that exceeded a heart rate variation index threshold). Patients in the second population were re-programmed to a rate-responsive pacing mode. After the re-programming to the rate-responsive pacing mode, patients in the second population were matched with patients in the first population except for the pacing mode. As illustrated by the first and second survival probability curves 701 and 702, patients in the second population had an improved survival probability relative to patients who remained in a non-rate-responsive pacing mode. Because the first and second populations included initially matched patients, the improved survival probability can be attributed to the particular rate-responsive pacing mode used.

FIG. 7 illustrates generally third and fourth survival probably curves 703 and 704 that correspond, respectively, to third and fourth populations. The third and fourth populations included patients who had heart rate variation indices that were less than a heart rate variation threshold index (e.g., the heart rate variation index for each patient in the third and fourth populations was less than about 0.7). Accordingly, patients in the third and fourth populations had relatively dynamic heart rates. The third and fourth populations included particular groups of patients who were initially matched to the first and second populations except for the heart rate variation indices of the patients.

In the example of FIG. 7, the third population remained in a non-rate-responsive pacing mode throughout the study, and the fourth population was re-programmed to a rate-responsive pacing mode. As illustrated in the example of FIG. 7, patient survival probability for particular patients with sufficiently dynamic heart rates can be about the same whether or not a rate-responsive pacing therapy is used.

To summarize, the example of FIG. 7 illustrates generally that particular patient populations with relatively high heart rate variation (e.g., corresponding to a relatively low heart rate variation index) can have a greatest survival probability. In particular high heart rate variation populations, rate-responsive pacing can be of little or no benefit to patient survival probability, although patients in such populations can benefit from rate-responsive pacing in other ways. Particular populations with relatively low heart rate variation (e.g., corresponding to a relatively high heart rate variation index) can generally have a lower survival probability than the particular populations with higher heart rate variation. Outcomes of particular populations with relatively low heart rate variations can sometimes be improved, however, such as by using a rate-responsive pacing therapy.

A survival probability can be improved for some patients who have low heart rate variability, such as by providing a rate-responsive pacing therapy. Enabling a rate-responsive pacing mode can influence particular patient outcomes by changing a patient's heart rate in response to a physiologic need. For example, a patient's heart rate and cardiac output can be increased in response to a physiologic need using a rate-responsive pacing mode. Enabling the rate-responsive pacing mode can, in some cases, increase a patient's heart rate variation and decrease the patient's heart rate variation index. Because higher heart rate variation and lower heart rate variation indices can be correlated with improved patient survival probability (see, e.g., the example of FIG. 7), the survival probability of some patients who receive rate-responsive pacing therapy can be improved.

Figure 8:
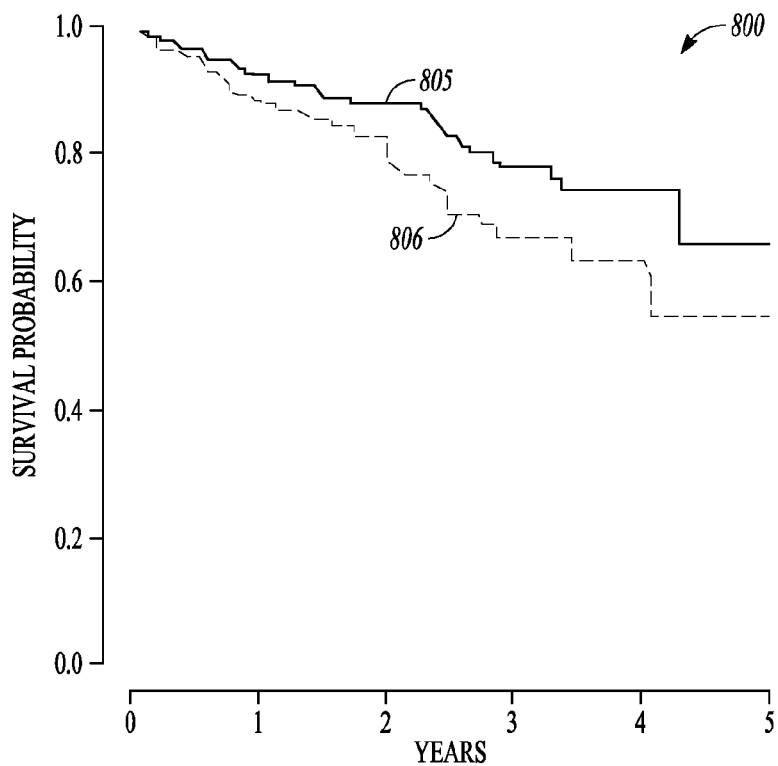
FIG. 8 illustrates generally an example that can include patient survival probability trends corresponding to different patient populations.
Figure 9:
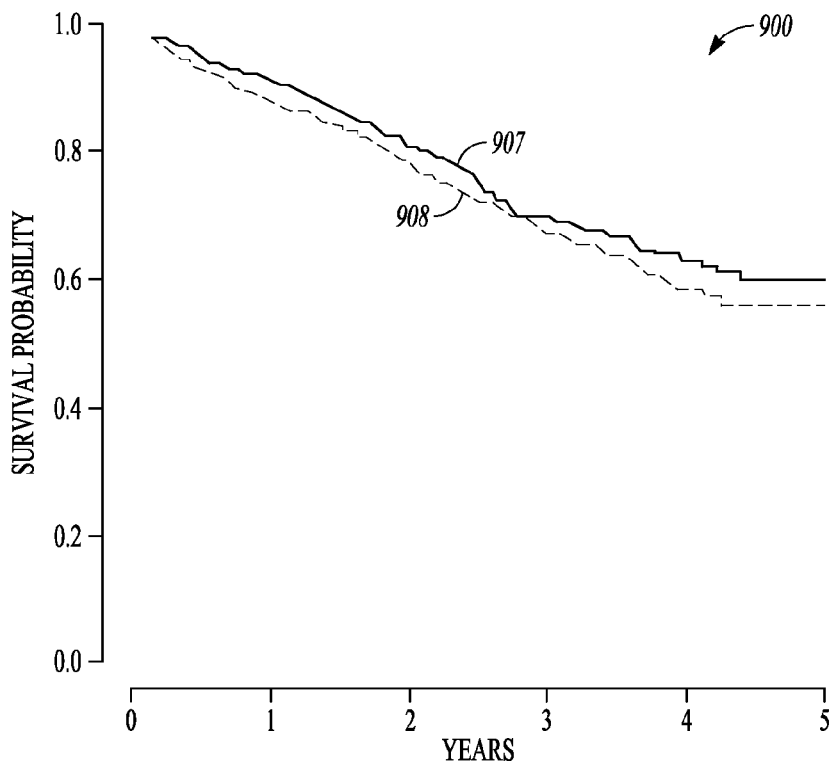
FIG. 9 illustrates generally an example that can include patient survival probability trends corresponding to different patient populations.

FIGS. 8 and 9 illustrate generally examples of actual patient data that show some distinct groups of patients receive no mortality benefit from a rate-responsive pacing mode, and some distinct groups of patients may possibly be negatively impacted by enabling a rate-responsive pacing mode.

FIG. 8 illustrates generally an example 800 of a study that shows rate-responsive pacing may possibly have a negative effect on patient survival for a particular population of patients. The example 800 includes information about particular fifth and sixth populations that were initially matched. The fifth and sixth populations included patients who had high heart rate variation (e.g., the patients had heart rate variation indices less than about 0.3).

In the example of FIG. 8, a fifth survival probability curve 805 corresponds to the fifth population, and a sixth survival probability curve 806 corresponds to the sixth population. The fifth population remained in a non-rate-responsive pacing mode throughout the study, and the sixth population was re-programmed to a rate-responsive pacing mode at the beginning of the study. Both the fifth and sixth populations received atrial pacing less than 30% of the time during the study. That is, less than 30% of the total number of heart beats were non-intrinsic beats. In this particular study, survival probability was negatively impacted for the particular patients who were re-programmed to the rate-responsive pacing mode as compared to the survival probability for the patients who remained in the non-rate-responsive pacing mode. Accordingly, to improve patient survival probability among patients who receive less than a threshold amount of pacing (e.g., less than a specified threshold number of paced beats), rate-responsive pacing can be contraindicated for patients with high heart rate variation. Patients with high heart rate variation can be identified by monitoring patient heart rate variation or patient heart rate variability, such as using a heart rate variability histogram or heart rate variation histogram to identify changes in patient heart rate over periods of time that exceed a single heart beat. Patients with high heart rate variation experience heart rates that are dynamic and change over time (see, e.g., the heart rate variation histogram 300 of FIG. 3A and the corresponding discussion herein).

FIG. 9 illustrates generally an example 900 of a study that shows rate-responsive pacing can have a neutral effect on patient survival for a particular population of patients. The example 900 includes information about particular seventh and eighth populations that were initially matched. The seventh and eighth populations included patients who had moderate heart rate variation (e.g., the patients had heart rate variation indices between about 0.3 and 0.7).

In the example of FIG. 9, a seventh survival probability curve 907 corresponds to the seventh population, and an eighth survival probability curve 908 corresponds to the eighth population. The seventh population remained in a non-rate-responsive pacing mode throughout the study, and the eighth population was re-programmed to a rate-responsive pacing mode at the beginning of the study. Survival probability for the patients who were re-programmed to the rate-responsive pacing was not significantly impacted compared to the survival probability for the patients who remained in the non-rate-responsive pacing mode. Accordingly, survival probability among patients with moderate heart rate variation can be substantially unaffected by rate-responsive pacing.

Multiple ranges of heart rate variation or heart rate variability can be used to provide a patient metric, such as can be used to indicate a particular patient therapy. For example, three heart rate variation ranges can be used: a low heart rate variation (e.g., corresponding to heart rate variation indices greater than about 0.7), a high heart rate variation (e.g., corresponding to heart rate variation indices less than about 0.3), and a moderate heart rate variation (e.g., corresponding to heart rate variation indices between about 0.3 and 0.7). A different or individualized therapy indication, or therapy recommendation, can correspond to one or more of the heart rate variation ranges.

Figure 10:
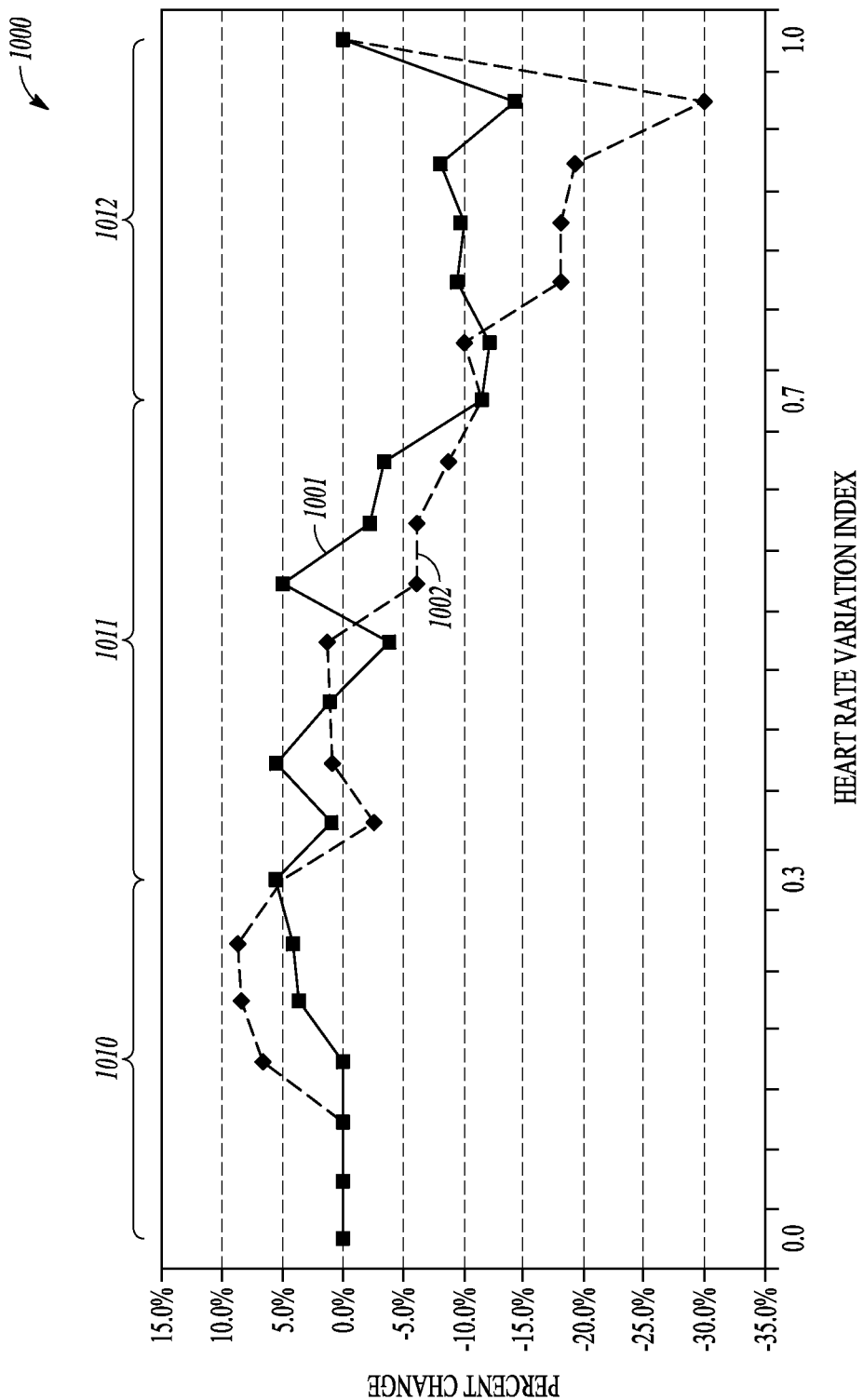
FIG. 10 illustrates generally an example that can include a relationship between a physiologic sensor type and a heart rate variation.

FIG. 10 illustrates generally an example 1000 that shows changes in heart rate variation when rate-responsive pacing is enabled for patients who receive any pacing therapy. The example 1000 includes a heart rate variation index along the x-axis, and a percent change in heart rate variation index along the y-axis. FIG. 10 illustrates a low heart rate variation index range 1010, a moderate heart rate variation index range 1011, and a high heart rate variation index range 1012.

In the example of FIG. 10, first and second heart rate variation trendlines 1001 and 1002 indicate average changes in heart rate variation index corresponding to different patient populations (e.g., each population comprises multiple patients). The first trendline 1001 corresponds to a population of patients whose pacemaker devices used accelerometer information to provide rate-responsive pacing therapies ("accelerometer patients"). The second trendline 1002 corresponds to a population of patients whose pacemaker devices used accelerometer and thoracic impedance information to provide rate-responsive pacing therapies ("blended patients").

In the low heart rate variation index range 1010 (e.g., corresponding to a heart rate variation index of less than about 0.3), both populations of patients experienced an increase in heart rate variation index. The blended patients experienced a greater increase in heart rate variation index throughout this range. For example, at a heart rate variation index of 0.20, the accelerometer patients experienced a variation index increase of about 4%, and the blended patients experienced a variation index increase of about 9%. Thus, the patients in the low heart rate variation index range 1010 experienced a decrease in heart rate variation (e.g., corresponding to poorer patient outcomes), although the decrease was relatively small. For example, even if an initial heart rate variability index of 0.20 changes by +9%, the resulting index of about 0.22 can be insignificant enough that a therapy change can be contraindicated.

Throughout the moderate heart rate variation index range 1011 (e.g., corresponding to a heart rate variation index of less than about 0.7 and greater than about 0.3), changes in heart rate variation index can be relatively small (e.g., less than about 10%). In the moderate heart rate variation index range 1011, no statistically significant difference is observed between the accelerometer patients and blended patients.

In the high heart rate variation index range 1012 (e.g., corresponding to a heart rate variation index of greater than about 0.7), however, there can be a significant difference between the accelerometer patients and the blended patients. For example, at a heart rate variation index of about 0.80, the accelerometer patients can experience a decrease in the index by about 10%. The blended patients, however, can experience a decrease in the index by about 18%. Accordingly, the accelerometer patients can have a resulting index of about 0.72, which can still be in the high heart rate variation index range 1012. The blended patients, however, can have a resulting index of about 0.66, which can be in the moderate heart rate variation index range 1011. Although both the accelerometer patients and the blended patients can benefit from rate-responsive pacing, the heart rate variation of the blended patients can be improved more than the heart rate variation of the accelerometer patients.

Overall, in the example of FIG. 10, the accelerometer patients experienced an average heart rate variation index improvement of about 7%. The blended patients experienced an average heart rate variation index improvement of about 15%. Thus, FIG. 10 shows that different types of sensors can effect different changes in heart rate variation index. When metabolic need is properly assessed, such as using one or more sensors, heart rate variation can be more effectively managed using a rate-responsive pacing therapy. In addition, FIG. 10 demonstrates that a magnitude of a heart rate variation response to rate-adaptive pacing can depend on a baseline heart rate variation index.

Figure 11:
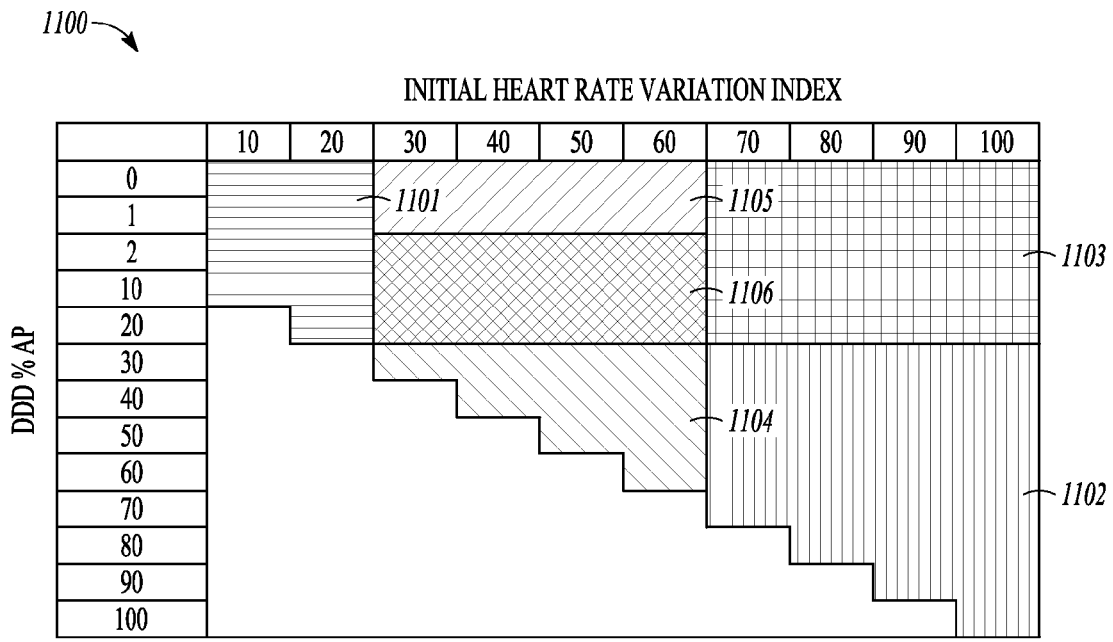
FIG. 11 illustrates generally an example that can include a relationship between an initial heart rate variation index and a percentage of atrial pacing events.

FIG. 11 illustrates generally an example 1100 of a relationship between an amount of pacing, a heart rate variation, and a patient survival probability. Along the horizontal axis, the example 1100 illustrates an initial heart rate variation index, such as corresponding to a patient who initially receives a non-rate-responsive pacing therapy. Along the vertical axis, the example 1100 illustrates a percentage of paced events or beats (e.g., paced atrial events). Several areas of the example 1100 correspond to different survival probabilities of particular patients who were reprogrammed from a non-rate-responsive pacing mode to a rate-responsive pacing mode after an initial time versus particular patients who remained in a non-rate-responsive pacing mode before and after the initial time.

The example 1100 illustrates generally that some particular patients or patient populations may receive a survival benefit by enabling and using a rate-responsive pacing mode, while other particular patients or patient populations may be negatively impacted by enabling and using a rate-responsive pacing mode. For example, as described in the example of FIG. 5, as a heart rate variation index increases, outcomes may be negatively impacted. As a heart rate variation index decreases, outcomes may be positively impacted. As described in the discussion of FIG. 10, enabling and using a rate-responsive pacing mode can have a greatest effect on a heart rate variation index (e.g., to increase or decrease a heart rate variation index) when a patient initially has a high heart rate variation index (e.g., in the example of FIG. 10, for an initial heart rate variation index of greater than about 0.7, a patient's heart rate variation index can be decreased by up to about 30% in response to enabling and using a rate-responsive pacing mode). Thus, the example 1100 shows that some particular patients can receive a positive survival benefit (see, e.g., second and third areas 1102 and 1003) by enabling a rate-responsive pacing mode, and other particular patients can be negatively impacted (see, e.g., the first area 1101) by enabling a rate-responsive pacing mode.

A first area 1101 of the example 1100 corresponds to a particular population of patients who have an initial heart rate variation index less than 0.3, and receive pacing less than 30% of the time. Patients in this population who received a rate-responsive pacing therapy after the initial time can have a lower survival probability relative to patients who remained in a non-rate-responsive pacing mode before and after the initial time.

A second area 1102 of the example 1100 corresponds to a particular population of patients who have an initial heart rate variation index greater than 0.7, and receive pacing more than 30% of the time. Patients in this population who received a rate-responsive pacing therapy after the initial time can have a substantially higher survival probability relative to patients who remained in a non-rate-responsive pacing mode before and after the initial time. Thus, a patient who has a high initial heart rate variation index and receives high amounts of atrial pacing (e.g., a patient whose heart rate is often at or near a lower rate limit of the patient's pacing therapy) can receive a benefit from a rate-responsive pacing therapy (see, e.g., FIG. 6 at 601 for an example of a particular patient whose survival probability can possibly be improved by providing a rate-responsive pacing therapy).

As illustrated in the example of FIG. 11, other particular populations can have intermediate survival probabilities. For example, a third area 1103 can correspond to a particular population of patients who have an initial heart rate variation index greater than 0.7, and receive pacing less than 30% of the time. Patients in the population corresponding to the third area 1103 and who received a rate-responsive pacing therapy after the initial time can have better outcomes than the particular patients corresponding to the first area 1101. However, patients in the population corresponding to the third area 1103 and who received a rate-responsive pacing therapy after the initial time can have a lower survival probability than the particular patients corresponding to the second area 1102 who also received a rate-responsive pacing therapy after the initial time. Thus, a patient who has a high initial heart rate variation index and receives low amounts of atrial pacing (e.g., a patient whose heart rate is often above a lower rate limit of the patient's pacing therapy) can receive a moderate benefit from a rate-responsive pacing therapy (see, e.g., FIG. 6 at 603).

Areas 1104, 1105, or 1106 of the example 1100 can similarly correspond to intermediate survival probabilities of particular patients who received a rate-responsive pacing therapy relative to patients who did not. In the areas corresponding to intermediate survival probabilities, pacing can be based on other methods or information, such as patient symptoms.

Figure 12:
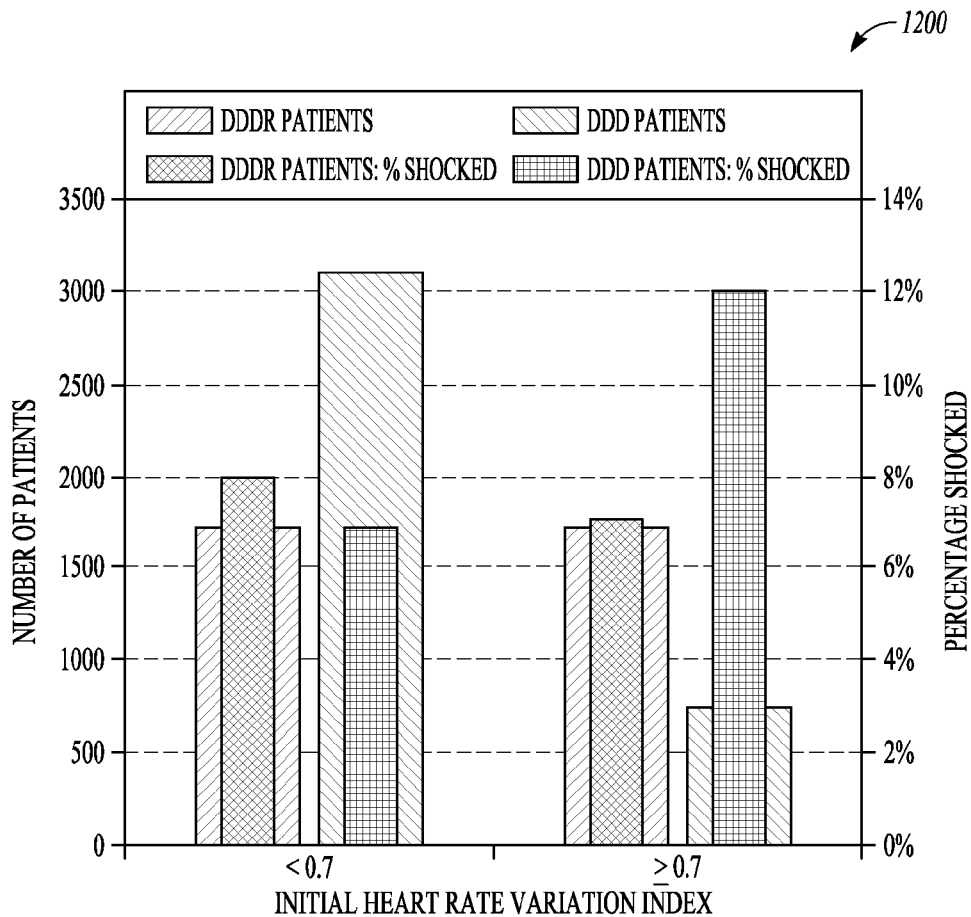
FIG. 12 illustrates generally an example that can include a relationship between a heart rate variation index and defibrillation shocks.

A heart rate variation can be used to identify particular patients at an increased risk of a cardiac arrhythmia or to identify a likelihood of a defibrillation shock therapy. FIG. 12 illustrates generally an example 1200 of a study of particular patients who had pacing and defibrillation devices that were operable for over one million beats (e.g., including intrinsic and non-intrinsic beats). In the example of FIG. 12, about the same number of patients who received a rate-responsive pacing therapy (DDDR patients) had high heart rate variation indices (e.g., indices greater than 0.7) as had lower heart rate variation indices (e.g., indices less than 0.7). In this study, the patients with high heart rate variation indices who had devices that operated in a rate-responsive pacing mode were not significantly more or less likely to receive a defibrillation shock than patients with low heart rate variation indices who had devices that operated in a rate-responsive pacing mode.

In the example of FIG. 12, about 3000 patients who received a non-rate-responsive pacing therapy (DDD patients) had low heart rate variation indices, and about 750 patients using non-rate-responsive pacing had high heart rate variation indices. However, the patients who received non-rate-responsive pacing therapy and had high heart rate variation indices received about 5% more defibrillation shocks than patients who received non-rate-responsive pacing therapy and had low heart rate variation indices. Thus, in some cases, patients with high heart rate variation indices can be more likely to receive a defibrillation shock therapy. Because shock therapy is generally provided in response to an identified arrhythmia, such as a tachycardia or fibrillation episode, low heart rate variation (e.g., corresponding to a high heart rate variation index) can be correlated with an increased risk of arrhythmias and treatment shocks. Thus, shock frequency can be reduced for some patients by pacing in a rate-responsive pacing mode based on heart rate variation information.

Various systems or devices, such as cardiac function management devices, can be used to identify a heart rate variability or a heart rate variation. An implantable device, such as an implantable cardiac function management device, such as can be configured to detect one or more type of cardiac arrhythmia, such as an atrial or ventricular fibrillation or tachycardia, can be further configured to identify a heart rate variability or a heart rate variation. In an example, a suitable implantable medical device can include an implantable defibrillator, pacemaker, or other cardiac rhythm or function management device with a defibrillation energy delivery mode.

Figure 13:
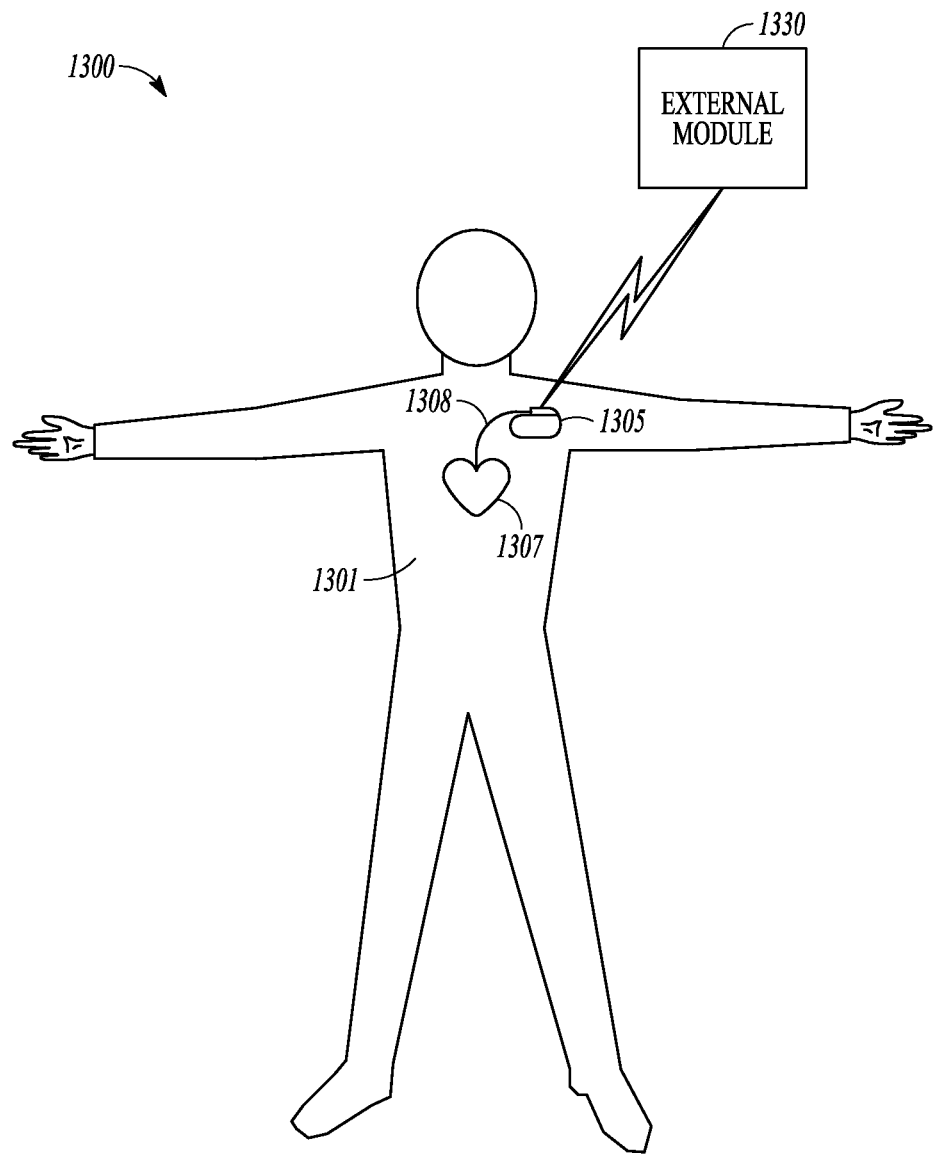
FIG. 13 illustrates generally an example of a patient assessment and therapy delivery system.

FIG. 13 illustrates generally an example of a portion of a system 1300 that can include an implantable medical device (IMD) 1305. The IMD 1305 can be configured to be implanted in a patient 1301. The system 1300 can include an external module 1330. The system 1300 can be configured to determine or use information about a heart rate variation or a heart rate variability, such as to provide a patient therapy or monitor a patient health status. The external module 1330 can include a local or remote programmer, such as can be used to process or share heart rate variability or heart rate variation information. The external module 1330 can include a handheld programmer or other programmer communicatively coupled to the IMD 1305. The external module 1330 can be configured to communicate with the IMD 1305 directly or indirectly (e.g., using another device such as a router, network repeater, etc.). The external module 1330 can be configured to communicate with or store information from multiple implanted or external devices.

The external module 1330 can be configured to send information to or receive information from the IMD 1305. The information can include programming information, subject data, device data, or instructions, alerts, or other information. The external module 1330 can be configured to communicate the sent or received information to a user or physician, such as by sending an alert (e.g., via email) of the status of the patient 1301 or the system 1300 components.

The IMD 1305 can be coupled to a patient heart 1307, such as using an implantable lead system 1308. The IMD 1305 can be coupled to the patient heart 1307 using wireless electrodes, subcutaneously placed electrodes, or other intravascularly-leadless systems. The IMD 1305 can include an electrostimulation therapy delivery circuit that can be coupled to the implantable lead system 1308 or other energy delivery system, such as to provide a rate-responsive pacing therapy to the heart 1307.

Figure 14:
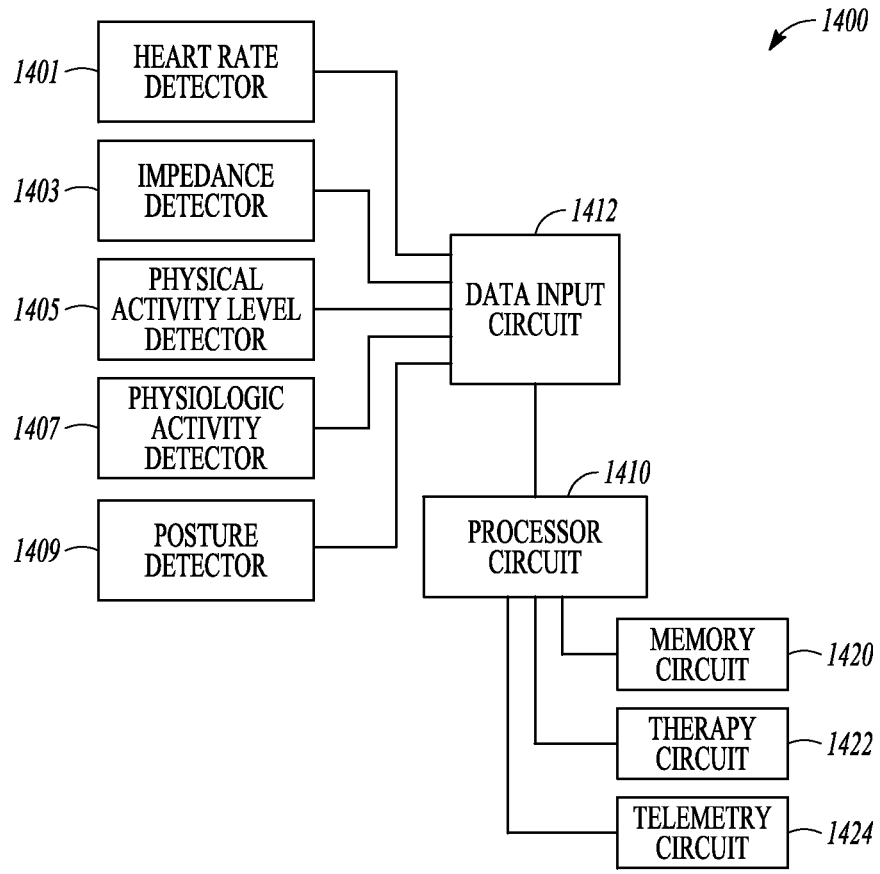
FIG. 14 illustrates generally an example of a system that can identify a heart rate variability or a heart rate variation.

FIG. 14 illustrates generally an example of a system 1400 that can be configured to identify a heart rate variability or a heart rate variation. In an example, all or a portion of the system 1400 can be included in or coupled to the IMD 1305 or the external module 1330. The system 1400 can include a processor circuit 1410, such as can be coupled to a data input circuit 1412. The data input circuit 1412 can be configured to receive physiologic information about a patient. For example, the data input circuit 1412 can be configured to receive physiologic information including, among other information, heart rate information from a heart rate detector 1401, impedance information from an impedance detector 1403, physical activity level information from a physical activity level detector 1405, physiologic activity information from a physiologic activity detector 1407, or posture information from a posture detector 1409.

The heart rate detector 1401 can include one or more electrodes disposed in or on a patient body and configured to provide an electrical signal representative of cardiac activity (e.g., an ECG signal). The heart rate detector 1401 can use the electrical signal representative of cardiac activity to determine a heart rate. For example, the heart rate detector 1401 can use an R-wave detection algorithm to identify R-wave peaks in an ECG. The data input circuit 1412 or the processor circuit 1410 can interpret the R-wave peaks and determine a patient heart rate. The heart rate detector 1401 can include other sensors or analysis modules configured to receive a physiologic signal and identify a heart rate. For example, the heart rate detector 1401 can include an accelerometer configured to provide information about mechanical cardiac activity.

The impedance detector 1403 can include a circuit configured to be coupled to one or more electrodes, such as disposed in or on a patient body. In an example, the electrodes can be placed in a patient thorax. The impedance detector 1403 can be configured to receive thoracic impedance information, such as can be used to determine information about, among other things, cardiac or respiratory activity. Information from the impedance detector 1403 can be interpreted by the processor circuit 1410, such as to determine a heart rate variability or a heart rate variation. For example, heart rate information can be determined using information received from the impedance detector 1403.

The physical activity level detector 1405 can include one or more sensors configured to receive information about a patient physical activity level. For example, the physical activity level detector 1405 can include an accelerometer, such as disposed in or on a patient body, and configured to sense patient movement. The physical activity level detector 1405 can provide an electrical signal representative of patient physical activity to the processor circuit 1410, such as via the data input circuit 1412. Information received from the physical activity level detector 1405 can be used to provide an indication of a patient metabolic need, such as can be used to initiate or adjust a rate-responsive pacing mode.

The physiologic activity detector 1407 can include one or more sensors configured to receive information about a patient physiologic activity. For example, the physiologic activity detector 1407 can be configured to receive information about neural activity, hemodynamics, or other physiologic changes in a patient body. Information from the physiologic activity detector 1407 can be used to determine a patient metabolic need, or to determine a heart rate variability or heart rate variation.

The posture detector 1409 can be configured to receive information about a posture status or posture change. For example, the posture detector 1409 can include one or more of an accelerometer or an impedance sensor that can be used to identify a particular patient posture (e.g., upright, supine, left supine, etc.). Information from the posture detector 1409 can be used to adjust a patient therapy, or can be used to determine a heart rate variability or heart rate variation. For example, a heart rate variability can be adjusted (e.g., weighted by a specified amount) when a patient is in a specified posture.

In the example of FIG. 14, the system 1400 can include one or more of a memory circuit 1420, a therapy circuit 1422, or a telemetry circuit 1424. The memory circuit 1420 can be configured to receive information about patient physiologic activity, such as information about a heart rate or other physiologic variable (e.g., a cardiac cycle interval, ECG morphology characteristic, etc.). In an example, the memory circuit 1420 can be configured to store information in a histogram (e.g., in a heart rate variation histogram).

The therapy circuit 1422 can include, among others, a pacing therapy circuit, a defibrillation therapy circuit, a neural modulation therapy circuit, or other circuit configured to provide an electrostimulation or other therapy to a patient body. The therapy circuit 1422 can include a combination of at least one of a right ventricular sensing channel, a right ventricular pacing channel, a left ventricular sensing channel, a left ventricular pacing channel, or an atrial sensing channel. A sensing channel can include a sense amplifier, and a pacing channel can include a pulse generator. Sensing and pacing channel(s) can be coupled to one or more electrodes, such as disposed on an electrode lead or elsewhere, such as disposed in or on a patient body. A lead can be configured to electrically couple a sense amplifier or pulse generator to an electrode, which can be configured to be located in a right ventricle, such as in the septal region, the free wall region, or another region of a right ventricle.

The therapy circuit 1422 can include one or more other pacing or sensing channels, such as an internal thoracic pacing or sensing channel configured to couple the processor circuit 1410 to an internal thoracic location external to the heart (e.g., using one or more leads, electrodes, pulse generators, or sense amplifiers). The internal thoracic pacing or sensing channel can be configured to send or receive information to or from a housing can electrode, located on the exterior housing of an implantable medical device in the internal thoracic location.

The processor circuit 1410, the memory circuit 1420, or the detectors 1401, 1403, 1405, 1407, and 1409, can be implantable or external components, or a combination of implantable and external components. For example, when at least a portion of the processor circuit 1410 is external, then the processor circuit 1410 can be communicatively coupled with the other components in the system 1400, such as using the telemetry circuit 1424. The telemetry circuit 1424 can be configured to communicate (e.g., wirelessly) with other devices or modules external to the system 1400. For example, the telemetry circuit 1424 can be configured to communicate information from the processor circuit 1410 to the external module 1330. The processor circuit 1410 can advantageously include an external processor circuit, such as for performing complex operations, such as to compute a variability index or a variation index. The memory circuit 1420 can advantageously include an external memory portion, such as for storing heart rate information or other physiologic variable information over time.

The processor circuit 1410, or an external portion of the processor circuit 1410 (e.g., in the external module 1330), can be configured to receive physiologic patient information and determine a heart rate variability or a heart rate variation. The processor circuit 1410 can receive heart rate information from the heart rate detector 1401. The processor circuit 1410 can use the heart rate information to determine a variability index or a variation index. The processor circuit 1410 can report the heart rate variability, the heart rate variation, or the indices, such as using an external module, or the processor circuit 1410 can use information about the heart rate variability, the heart rate variation, or the indices, to configure the therapy circuit 1422, such as by updating a therapy parameter. For example, the processor circuit 1410 can use information about a heart rate variation index to enable the physical activity level detector 1405 and adjust the therapy circuit 1422, such as to initiate a rate-responsive pacing mode.

Figure 15:
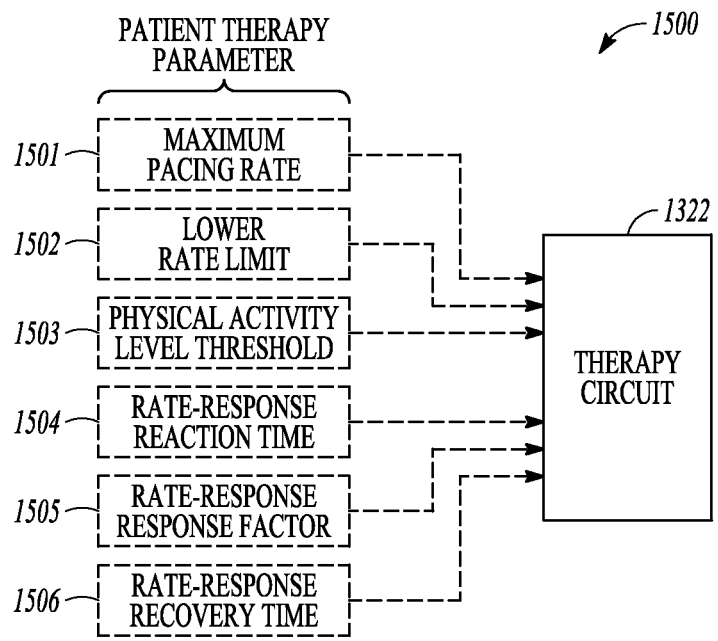
FIG. 15 illustrates generally an example of a therapy circuit and multiple therapy parameters.

FIG. 15 illustrates generally an example that can include using the therapy circuit 1322 with a therapy parameter. The processor circuit 1410 and/or the therapy circuit 1422 can use information about a determined heart rate variability or heart rate variation to adjust a therapy parameter. Using an adjusted therapy parameter, the therapy circuit 1422 can provide an updated patient therapy. For example, the processor circuit 1410 can update a maximum pacing rate 1501 using information about the determined heart rate variability. The maximum pacing rate can control a maximum rate at which a pacemaker provides a pacing energy to a heart (e.g., 100 electrostimulations per minute). The therapy circuit 1422 can use the updated maximum pacing rate to provide a pacing therapy. In an example, when information about a patient heart rate variation indicates a high patient heart rate variation (e.g., corresponding to a low heart rate variation index), then the maximum pacing rate 1501 can be increased, such as by an amount corresponding to the patient heart rate variation index (e.g., the maximum pacing rate 1501 can be a function of a heart rate variation index or a heart rate variability index).

Using information about the determined heart rate variability or heart rate variation, the processor circuit 1410 can update a lower rate limit 1502, such as to control a rate at which a pacemaker begins to provide a pacing therapy to the heart 1307. For example, when the lower rate limit 1502 is 60 bpm, the therapy circuit 1422 can provide a pacing therapy when a patient heart rate is less than about 60 bpm (e.g., such as determined automatically using the heart rate detector 1401). In an example, when information about a patient heart rate variation indicates a low patient heart rate variation (e.g., corresponding to a high heart rate variation index), then the lower rate limit 1502 can be decreased, such as by an amount corresponding to the patient heart rate variation index (e.g., the lower rate limit 1502 can be a function of a heart rate variation index or a heart rate variability index).

Using information about the determined heart rate variability or heart rate variation, the processor circuit 1410 can update a physical activity level threshold 1503. The physical activity level threshold 1503 can control a patient physical activity level at which a pacing energy is initiated or adjusted. For example, in a rate-responsive pacing mode, the therapy circuit 1422 can use the physical activity level threshold 1503 to determine when to provide an increased pacing rate. For example, physical activity level information (e.g., received using the physical activity level detector 1405) can be used to determine an increased metabolic need for cardiac output. The processor circuit 1410 and/or the therapy circuit 1422 can interpret the increased metabolic need and the physical activity level threshold 1503 to determine whether a pacing rate can be adjusted.

In an example, when information about a patient heart rate variation indicates a low patient heart rate variation (e.g., corresponding to a high heart rate variation index), then the physical activity level threshold 1503 can be decreased, such as to initiate a pacing therapy in response to lower levels of patient physical activity. The physical activity level threshold 1503 can be increased or decreased by an amount corresponding to the patient heart rate variation index (e.g., the physical activity level threshold 1503 can be a function of a heart rate variation index or a heart rate variability index).

Using information about the determined heart rate variability or heart rate variation, the processor circuit 1410 can update a rate-response reaction time 1504. The rate-response reaction time 1504 can control how quickly a pacing rate increases. For example, in response to a need for additional cardiac output, the therapy circuit 1422 can initiate rate-responsive pacing at a rate that gradually increases over time. For example, the therapy circuit 1422 can control a patient pacing transition from 60 bpm to 100 bpm using the rate-response reaction time, such as in response to a detected change in a patient physical activity level.

In an example, when information about a patient heart rate variation indicates a low patient heart rate variation (e.g., corresponding to a high heart rate variation index), then the rate-response reaction time 1504 can be decreased, such as to more rapidly initiate a pacing therapy, such as at a higher pacing rate, in response to patient physical activity. The rate-response reaction time 1504 can be increased or decreased by an amount corresponding to the patient heart rate variation index (e.g., the rate-response reaction time 1504 can be a function of a heart rate variation index or a heart rate variability index).

Using information about the determined heart rate variability or heart rate variation, the processor circuit 1410 can update a rate-response response factor 1505 to control a pacing rate as a function of a patient physical activity level. For example, the rate-response response factor 1505 can control how aggressively a heart rate is paced in response to a specified physical activity level. In an example, when information about a patient heart rate variation indicates a low patient heart rate variation (e.g., corresponding to a high heart rate variation index), then the rate-response response factor 1505 can be increased, such as to more aggressively pace a patient heart in response to patient physical activity. The rate-response response factor 1505 can be increased or decreased by an amount corresponding to the patient heart rate variation index (e.g., the rate-response response factor 1505 can be a function of a heart rate variation index or a heart rate variability index).

In an example, the processor circuit 1410 can update a rate-response recovery time 1506. The rate-response recovery time can control a rate at which a pacing rate decreases from an elevated pacing rate (e.g., a maximum pacing rate) to a lower or nominal pacing rate (e.g., a lower rate limit). For example, the processor circuit 1410 can identify a reduced need for cardiac output, and in response, the therapy circuit 1422 can use the rate-response recovery time 1506 to control a transition from a higher heart rate to a lower heart rate. The therapy circuit 1422 or the processor circuit 1410 can use the rate-response recovery time 1506 to control a heart rate transition when a patient physical activity level falls below a specified threshold physical activity level.

In an example, when information about a patient heart rate variation indicates a low patient heart rate variation (e.g., corresponding to a high heart rate variation index), then the rate-response recovery time 1506 can be increased, such as to decrease the rate at which an elevated pacing rate returns to a lower or nominal pacing rate, such as after a period of increased patient physical activity. The rate-response recovery time 1506 can be increased or decreased by an amount corresponding to the patient heart rate variation index (e.g., the rate-response recovery time 1506 can be a function of a heart rate variation index or a heart rate variability index).

Figure 16:
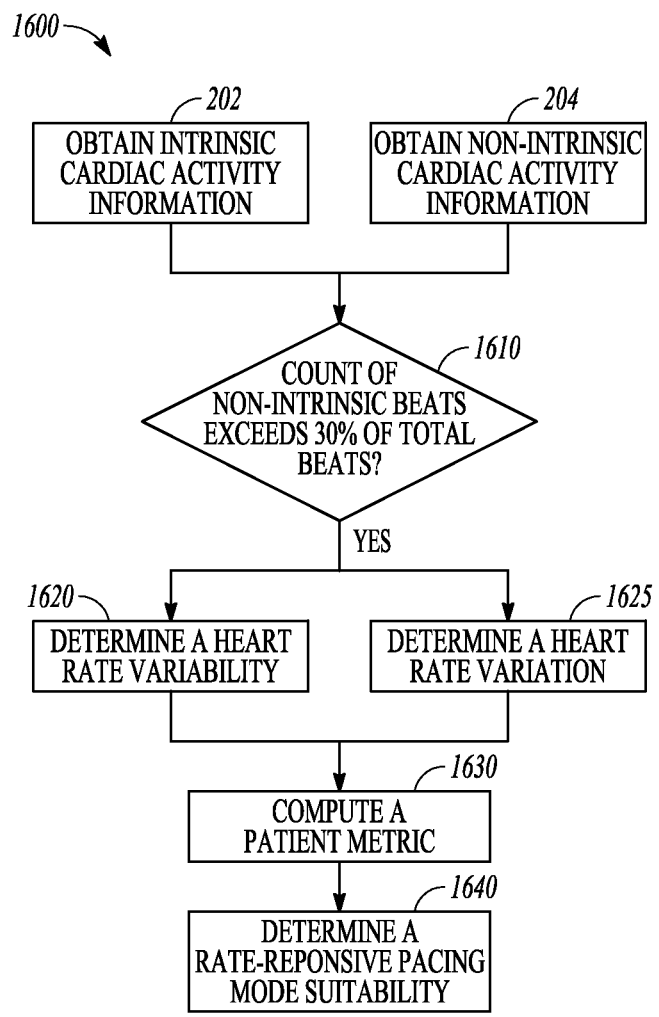
FIG. 16 illustrates generally an example that can include computing a patient metric or determining a rate-responsive pacing mode suitability.

The systems 1300, 1400, or 1500, among others, can be used to determine a heart rate variation or a heart rate variability. FIG. 16 illustrates generally an example 1600 that can include using a preliminary filter at 1610 to decide whether to determine a heart rate variability or a heart rate variation. In example 1600, at 202, intrinsic cardiac activity information can be obtained, such as according to the discussion of FIG. 2 at 202, and at 204, non-intrinsic cardiac activity can be obtained, such as according to the discussion of FIG. 2 at 204. The intrinsic and non-intrinsic cardiac activity information can be obtained using, among other things, the systems 1300, 1400, or 1500, such as using the heart rate detector 1401, the impedance detector 1403, the physiologic activity detector 1407, or some other detector or sensor configured to provide cardiac activity information to the processor circuit 1410.

Determining a heart rate variability or heart rate variation can be an intensive task because, for example, the determination can consume device resources (e.g., in the IMD 1305). In addition, referring to FIG. 11, various patient health outcomes can be expected depending, for example, on whether a patient receives a specified amount of pacing therapy. Accordingly, at 1610, the obtained cardiac activity information can be assessed to decide whether to determine a heart rate variability or a heart rate variation.

At 1610, information about intrinsic and non-intrinsic cardiac activity can be used to determine whether a heart rate variability or heart rate variation should be determined. When a count of non-intrinsic patient heart beats exceeds a threshold percentage of a total number of counted patient heart beats, a heart rate variability or a heart rate variation can be determined, such as using the processor circuit 1410. For example, if the count of non-intrinsic beats exceeds the threshold percentage of the total beats (e.g., 30%), then a heart rate variability can be determined at 1620, or a heart rate variation can be determined at 1625. Other preliminary filters can be applied at 1610. For example, if a count of a specified QT interval (e.g., a QT interval that corresponds to a paced event) exceeds a threshold count, then a heart rate variability can be determined at 1620.

At 1620 or 1625, a heart rate variability or heart rate variation can be determined, such as using the processor circuit 1410. The heart rate variability or heart rate variation can be determined using stored information about cardiac activity, such as stored in the memory circuit 1420. The heart rate variability can be determined at 1620 using stored cardiac activity information indicative of a patient heart rate. For example, decreasing QT interval can be correlated with increasing heart rate. The processor circuit 1410 can use information about a patient QT interval (e.g., received using one or more electrodes coupled to the implantable medical device 1305) to determine the heart rate variability at 1620. Other intra-beat variables can be used as well. An intrinsic QT interval can be distinguished from a non-intrinsic QT interval, such as by identifying outliers among adjacent QT intervals or in QT interval trends.

At 1630, information about the determined heart rate variability or heart rate variation can be used to compute a patient metric. The patient metric can include, among other things, a patient health status, a patient risk profile, a patient therapy indication, or a patient survival probability. The patient metric can include a heart rate variability index or a heart rate variation index. A patient metric can be computed at 1630 at regular intervals, or upon an occurrence of a specified event (e.g., after or during a drug therapy regimen, at night time, etc.). A series of patient metrics can be compared, such as to provide an indication of whether a patient health status has changed. For example, a worsening heart rate variability (e.g., corresponding to a heart rate variability that is lessening over time) can be an indication that an intervention is required, such as a change in a patient therapy.

At 1640, a rate-responsive pacing mode suitability can optionally be determined, such as using the processor circuit 1410 to interpret the patient metric. The processor circuit 1410 can use a patient metric to provide a rate-responsive pacing mode suitability indication. The processor circuit 1410 can provide an indication to initiate a rate-responsive pacing mode when a heart rate variability index is high, such as greater than about 0.7. The processor circuit 1410 can provide an indication to terminate or suspend a rate-responsive pacing mode when a heart rate variability index is low, such as less than about 0.3. An operating mode of the IMD 1305 can be programmed using the suitability information. For example, the processor circuit 1410 can use the suitability to provide instructions to the therapy circuit 1422 about whether to use a rate-responsive pacing mode.

Pacing therapies other than rate-responsive pacing can be used to affect a heart rate variability or a heart rate variation. For example, if a variability index or a variation index exceeds a specified threshold index, a pacing rate can be intermittently increased, such as until the variability index or the variation index is reduced to a sub-threshold level. Pacing can be varied, such as by mimicking natural patient circadian or like rhythms to improve a heart rate variability or heart rate variation. These therapy techniques, among others, can be used to improve a heart rate variation or heart rate variability, and can be applied such as to prevent arrhythmias (e.g., after a first shock), or after a detected ischemic event.

Information about a heart rate variation or heart rate variability can be used to initiate or adjust other therapies that can impact heart rate variation or heart rate variability. For example, a drug therapy can be initiated or updated (e.g., a dosage can be changed) when a heart rate variation or heart rate variability does not change in response to an initial therapy (e.g., a rate-adaptive pacing therapy). In an example, a neural stimulation therapy (e.g., a vagus nerve electrostimulation therapy) can be initiated or adjusted using information about a heart rate variation or heart rate variability.

Figure 17:
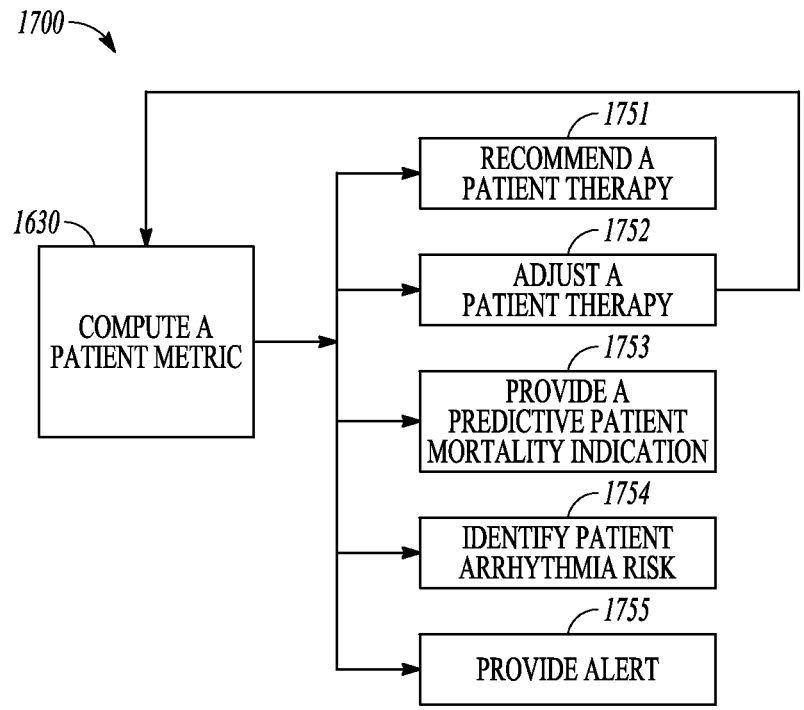
FIG. 17 illustrates generally an example that can include using a patient metric.

FIG. 17 illustrates generally an example 1700 that can include using a patient metric. At 1630, a patient metric can be computed, such as using the processor circuit 1410, such as described herein, such as with respect to the example of FIG. 16. The patient metric can include, among other things, a heart rate variability or variability index, or a heart rate variation or variation index.

At 1751, the patient metric can be used to recommend a patient therapy. For example, at 1751, a rate-responsive pacing recommendation can be provided. The patient therapy can be recommended and implemented automatically, such as using the processor circuit 1410 and the therapy circuit 1422. At 1751, recommending the patient therapy can include reporting the recommendation to a patient, clinician, or other caregiver, such as using the external module 1330. The clinician or other caregiver, or patient, can use the external module 1330 to respond to the therapy recommendation, such as by providing therapy parameters or other instructions to the IMD 1305. A specified pacing protocol, or pacing therapy parameter, can be implemented and/or executed, such as automatically in response to the computed patient metric.

At 1751, recommending a patient therapy can include recommending a cardiac function management device, such as a CRT or ICD device. For example, a heart rate variation can be determined at 1625 or 225, such as using a Holter monitor or other medical device configured to monitor a patient heart rate over time. The processor circuit 1410 can receive information about the patient heart rate, compute and interpret a patient metric, and recommend the patient therapy at 1751, such as including a therapy recommendation that the Holter patient receive a pacemaker (e.g., a pacemaker with a rate-responsive pacing mode).

At 1752, the patient metric computed at 1630 can be used to adjust a patient therapy. For example, the metric can be used to adjust a pacing mode for a cardiac pacing therapy, such as by enabling or disabling a rate-responsive pacing mode. Adjusting a patient therapy at 1752 can include adjusting a patient therapy parameter. For example, a maximum pacing rate 1501, a lower rate limit 1502, a physical activity level threshold 1503, a rate-response reaction time 1504, a rate-response response factor 1505, a rate-response recovery time 1506, or a therapy electrostimulation parameter, among other therapy parameters, can be adjusted, such as using information about the computed metric. One or more other therapies or therapy parameters can be adjusted using the heart rate variability, such as an electrostimulation electrode configuration, or a therapy reporting parameter.

A feedback loop can be established to compute or update a patient metric, such as after adjusting a patient therapy at 1752. A heart rate variability or heart rate variation can be determined, a patient metric can be computed (e.g., at 1630), and a patient therapy parameter can be adjusted (e.g., at 1752). After a specified duration, or in response to an observed change in patient physiologic activity, a patient metric can be re-computed or updated. The re-computed or updated patient metric can be used to further adjust the patient therapy, such as using the same therapy parameter or a different therapy parameter.

When a low heart rate variability or low heart rate variation is determined, one or more therapy parameters can be updated or adjusted. For example, adjusting a patient therapy at 1752 can include toggling a rate-response response factor 1505 to optimize a pacing therapy (e.g., to increase a heart rate variability or variation), such as using the feedback loop. The rate-response reaction time 1504 can be decreased, the rate-response response factor 1505 can be increased, or a rate-response recovery time 1506 can be increased, such as to increase or otherwise improve the heart rate variability or heart rate variation.

Physiologic patient information (such as described below in the example of FIG. 18) can be used to assess a patient therapy or further adjust a patient therapy parameter in a feedback loop. For example, a respiration sensor can be used to provide information about respiration trends or apnea events. Such information can be used to adjust or update the patient therapy at 1752. For example, a reduction in a number of apnea events can confirm that a rate-responsive pacing mode is effective, or an increase in a number of apnea events can indicate a need to adjust a therapy parameter.

At 1753, the patient metric computed at 1630 can be used to provide a predictive patient mortality indication. For example, information about the patient metric and information about a device operating mode can be used (see, e.g., FIG. 7). A predictive patient mortality indication can include a patient survival probability. A high patient survival probability can correspond to a particular patient metric, such as a high heart rate variability (e.g., or a low heart rate variability index). A high patient survival probability can be associated with high heart rate variability, such as when a patient receives a rate-responsive pacing therapy. A low patient survival probability can be associated with a low heart rate variability (e.g., or a high heart rate variability index). A low patient survival probability can be associated with low heart rate variability, such as when a patient receives a non-rate-responsive pacing therapy.

At 1754, the patient metric computed at 1630 can be used to identify a patient risk for a cardiac arrhythmia. For example, heart rate variability, such as in combination with one or more other patient variables (e.g., pacing mode), can be used to identify an elevated risk for a cardiac arrhythmia. In an example, such as illustrated in FIG. 12, patients with low heart rate variability (e.g., patients with high heart rate variability indices) who receive non-rate-responsive pacing therapy can be at an elevated risk for a cardiac arrhythmia as compared to patients with high heart rate variability who receive non-rate-responsive pacing therapy.

At 1755, an alert can be provided, such as using the IMD 1305 or the external module 1330. Providing the alert at 1755 can include providing information about the patient metric, or about one or more other patient characteristics, such as a patient heart rate variability, variability index, heart rate variation, or variation index. The alert can be provided using an IMD interrogator or programmer, or using the IMD itself, such as to alert a patient or caregiver of a change in a patient health status, or to indicate a need for a particular therapy.

Figure 18:
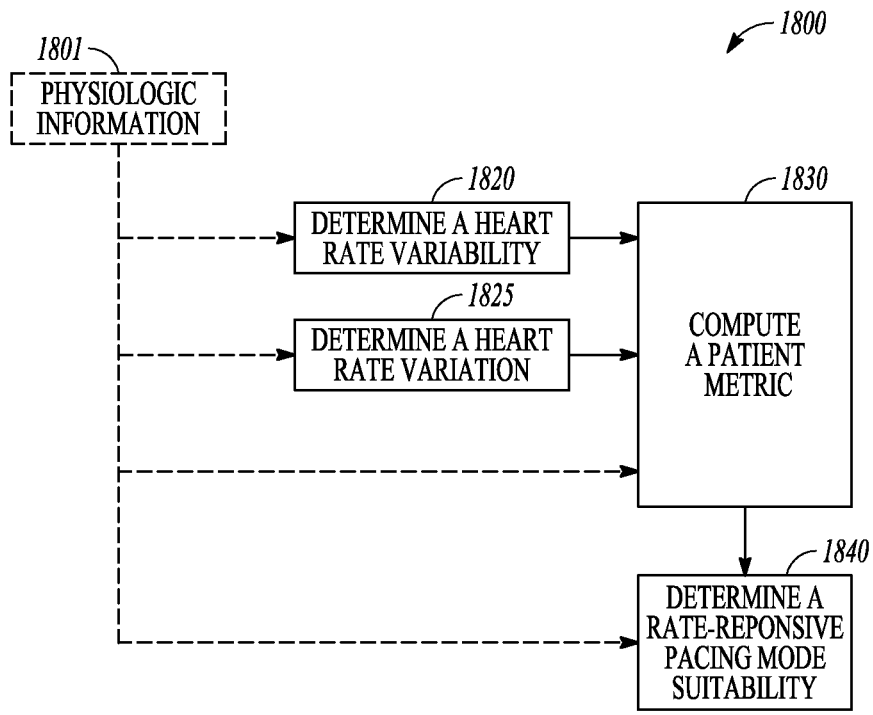
FIG. 18 illustrates generally an example that can include using physiologic information.

In addition to cardiac activity information, other physiologic information can be used or considered when determining a heart rate variability, a heart rate variation, or when computing a patient metric. FIG. 18 illustrates generally an example 1800 that can include determining a heart rate variability, a heart rate variation, or computing a patient metric, such as using other physiologic information.

In the example 1800, physiologic information 1801 can include physiologic patient information, such as can be received or determined using the detectors 1401, 1403, 1405, 1407, or 1409, among others. For example, the physiologic information 1801 can include patient posture information, such as received using the posture detector 1409.

At 1820, a heart rate variability can be determined, such as according to the discussion of FIG. 16 at 1620, such as using the physiologic information 1801. At 1825, a heart rate variation can be determined, such as according to the discussion of FIG. 16 at 1625, such as using the physiologic information 1801. At 1830, a patient metric can be computed, such as according to the discussion of FIG. 16 at 1630, such as using the physiologic information 1801.

At 1820, the heart rate variability can be determined using the physiologic information 1801 to validate or stratify the heart rate variability. For example, a particular determined heart rate variability can be valid for specified patient postures. Accordingly, the processor circuit 1410 can use physiologic information 1801 about a patient posture (e.g., received using the posture detector 1409) to determine a validity of a determined heart rate variability. A heart rate variation, such as determined at 1825, can be similarly validated or stratified using the physiologic information 1801. A series of heart rate variations can be determined at 1825, such as corresponding to different patient postures. For example, a first heart rate variation can be determined at 1825 for a patient in an upright posture (e.g., during daytime activities), and a second heart rate variation can be determined at 1825 for the same patient in a supine posture (e.g., during sleep periods).

Information from one or more other detectors or sensors can additionally or alternatively be used to validate or stratify a heart rate variation or a heart rate variability. For example, information about patient autonomic tone can be used, including information about baroreflex sensitivity (BRS) or muscle sympathetic nerve activity (MSNA). Information about a patient physical activity level or respiratory rate can be used.

At 1830, the patient metric can be computed using the patient posture information. For example, a first patient metric (e.g., a first variability index) can be computed that corresponds to a determined heart rate variability and to a first patient posture. A second patient metric (e.g., a second variability index) can be computed that corresponds to the same determined heart rate variability and to a second patient posture. In an example, a patient metric can include a heart rate variability index threshold, and the threshold can be differently valued depending on the patient's posture. For example, a first heart rate variability index threshold can be used when the patient is in a first posture (e.g., an upright posture), and a second heart rate variability index threshold can be used when the patient is in a second posture (e.g., a supine posture).

At 1840, a rate-responsive pacing mode suitability can optionally be determined using the physiologic information 1801. For example, a rate-responsive pacing mode suitability can be determined using the heart rate variability determined at 1620 and posture information, such as provided using the posture detector 1409. In an example, a rate-responsive pacing mode suitability can vary with patient posture. For example, a rate-responsive pacing mode can be indicated in a first patient posture (e.g., in an upright posture), and a rate-responsive pacing mode can be contraindicated in a second patient posture (e.g., in a supine posture).

Figure 19:
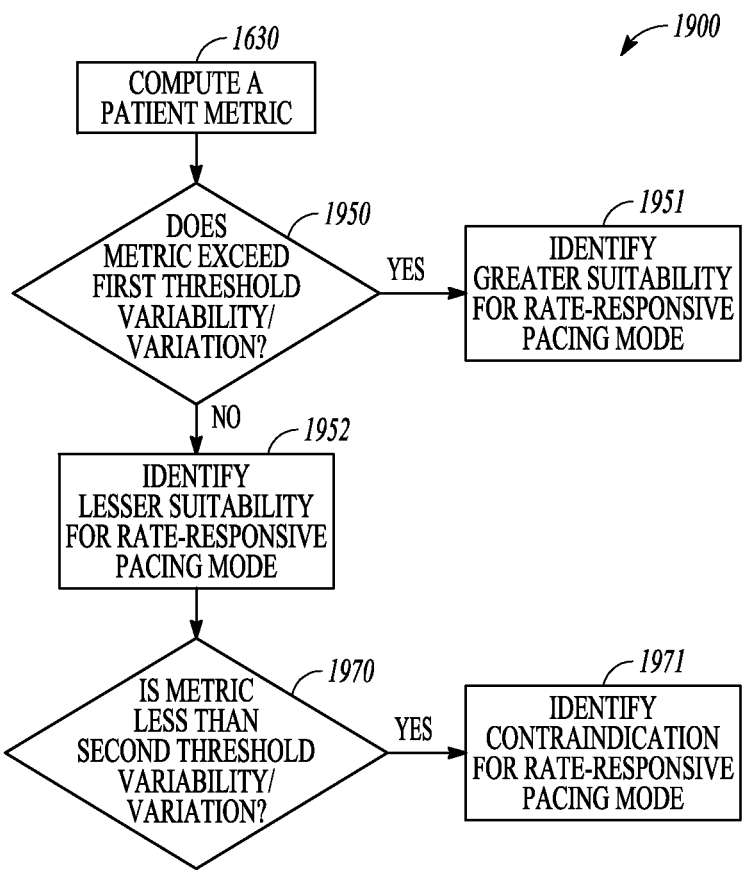
FIG. 19 illustrates generally an example that can include identifying a suitability for a rate-responsive pacing mode.

Identifying a rate-responsive pacing mode suitability can include assessing a magnitude of heart rate variability or heart rate variation. FIG. 19 illustrates generally an example that can include comparing a heart rate variability or heart rate variation to a threshold variability or variation, such as using the processor circuit 1410. At 1630, a patient metric can be computed, such as including a heart rate variability or variability index, or a heart rate variation or variation index. At 1950, the metric can be assessed to determine whether a heart rate variability or heart rate variation exceeds a threshold variability or variation. For example, a heart rate variability index can be compared to a first threshold variability index (e.g., 0.7). If the heart rate variability index exceeds the first threshold variability index, a greater suitability for a rate-responsive pacing mode can be identified at 1951. If the heart rate variability index is less than the first threshold variability index, a lesser suitability for the rate-responsive pacing mode can be identified at 1952.

The patient metric threshold, heart rate variability or variability index thresholds, or the heart rate variation or variation index thresholds described in this document can be pre-determined or default thresholds, or can be population-specific thresholds. For example, different thresholds can be used for patients with different disease characteristics, or for patients of different ages, among other distinguishing characteristics. A threshold can be a patient-specific threshold, such as can be automatically or iteratively determined using a therapy feedback loop, or determined manually by a physician or other caregiver (e.g., such as can be provided to the processor circuit 1410 using the external module 1330).

At 1970, if the lesser suitability was identified at 1952, the metric can be compared to a second threshold. If the metric is less than the second threshold, a contraindication for a rate-responsive pacing mode can be identified at 1971. For example, referring again to FIG. 10, when a heart rate variation index is less than a threshold index (e.g., corresponding to the low heart rate variation index range 1010), a heart rate variation can be worsened by using a rate-responsive pacing mode. If, at 1970, the metric is less than the first threshold and more than the second threshold, no determination can be made about a suitability for a rate responsive-pacing mode.

Figure 20:
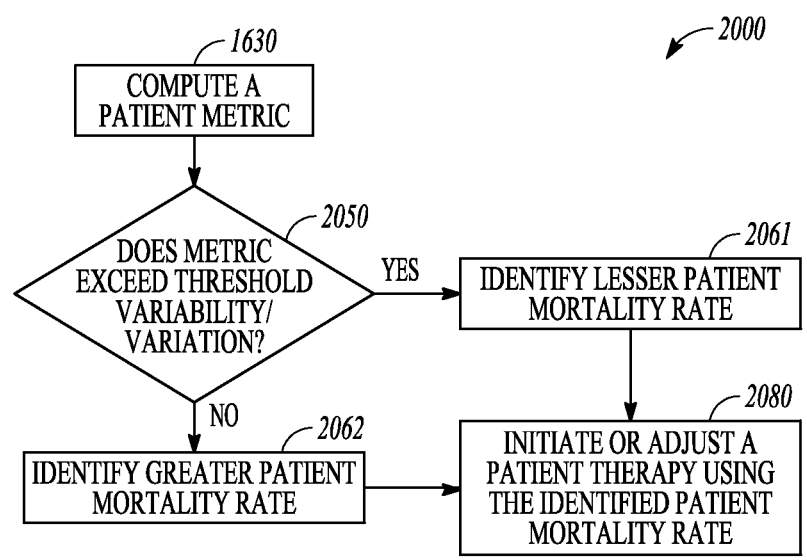
FIG. 20 illustrates generally an example that can include identifying a mortality rate.

Information about a patient metric, such as including information about a heart rate variability or variability index, or a heart rate variation or variation index, can be used to identify a patient mortality risk or a patient survival probability. FIG. 20 illustrates generally an example 2000 that can include using a patient metric to identify a patient mortality rate.

In the example of FIG. 20, at 1630, a patient metric can be computed, such as including a heart rate variability or variability index, or a heart rate variation or variation index, such as according to the discussion of FIG. 16, above. At 2050, the metric can be assessed to determine whether a heart rate variability or heart rate variation exceeds a threshold variability or variation. For example, if the metric (e.g., a heart rate variability) exceeds the threshold variability, a lesser patient mortality rate can be identified at 2061. A lesser patient mortality rate can correspond to an improved patient survival probability. If the metric is less than the threshold variability, a greater patient mortality rate can be identified at 2062. In an example, in response to the identified greater or lesser mortality rate, a patient therapy can be initiated or adjusted at 2080. For example, a rate-responsive pacing mode can be initiated or terminated, or a pacing therapy parameter can be adjusted, such as described above in the discussion of FIG. 17 at 1752.

Various Notes & Examples

Example 1 can include or use subject matter (such as an apparatus, a method, a means for performing acts, or a device readable medium including instructions that, when performed by the device, can cause the device to perform acts), such as can include or use a data input circuit configured to receive information indicative of a patient heart rate including information about both intrinsic and non-intrinsic patient heart beats, a memory circuit configured to store information about the patient heart rate over time, or a processor circuit, coupled to the memory circuit. In Example 1, the processor circuit can be configured to determine a heart rate variation using the stored information about the patient heart rate over time, wherein the determined heart rate variation can be indicative of a number of both intrinsic and non-intrinsic patient heart beats within a specified heart rate range. In Example 1, the processor circuit can be configured to compute a patient metric using the determined heart rate variation indicative of a number of both the intrinsic and non-intrinsic patient heart beats within the specified heart rate range.

Example 2 can include, or can optionally be combined with the subject matter of Example 1 to optionally include, the processor circuit configured to determine a rate-responsive pacing mode suitability indication for the patient using the computed patient metric.

Example 3 can include, or can optionally be combined with the subject matter of Example 2 to optionally include, the processor circuit configured to identify a lesser suitability for the rate-responsive pacing mode for the patient when the heart rate variation is at a first heart rate variation value, and identify a greater suitability for the rate-responsive pacing mode for the patient when the heart rate variation is at a second heart rate variation value that is less than the first heart rate variation value.

Example 4 can include, or can optionally be combined with the subject matter of one or any combination of Examples 2 or 3 to optionally include, the processor circuit configured to determine whether a count of the patient's non-intrinsic heart beats exceeds a specified portion of a total count of the patient's intrinsic and non-intrinsic heart beats during a specified period, and, when the count of the patient's non-intrinsic heart beats exceeds the specified portion of the total count of the patient's intrinsic and non-intrinsic heart beats during the specified period, determine the rate-responsive pacing mode suitability indication for the patient.

Example 5 can include, or can optionally be combined with the subject matter of one or any combination of Examples 2 through 4 to optionally include, a physiologic sensor configured to provide a signal indicative of the patient's metabolic need for a particular level of cardiac output. The rate-responsive pacing mode can be capable of automatically adjusting a patient pacing rate as a function of a variation in the signal indicative of the patient's metabolic need for the particular level of cardiac output.

Example 6 can include, or can optionally be combined with the subject matter of Example 5 to optionally include, the physiologic sensor configured to provide the signal indicative of the patient's metabolic need, wherein the physiologic sensor comprises an impedance sensor configured to provide a signal indicative of the patient's respiration status and/or an accelerometer configured to provide a signal indicative of the patient's physical activity level.

Example 7 can include, or can optionally be combined with the subject matter of one or any combination of Examples 1 through 6 to optionally include, the memory circuit configured to store the information about the patient heart rate in a heart rate histogram bin corresponding to a patient heart rate range. In Example 7, the processor circuit can be configured to determine the heart rate variation using information about the heart rate histogram.

Example 8 can include, or can optionally be combined with the subject matter of Example 7 to optionally include, the processor circuit configured to determine the heart rate variation using a morphology or geometric characteristic of the heart rate histogram.

Example 9 can include, or can optionally be combined with the subject matter of one or any combination of Examples 1 through 8 to optionally include, the processor circuit configured to compute, as the patient metric, a predictive patient mortality indication using the determined heart rate variation.

Example 10 can include, or can optionally be combined with the subject matter of Example 9 to optionally include, the processor circuit configured to identify a lesser patient mortality rate for the patient when the heart rate variation is at a first heart rate variation value, and identify a greater patient mortality rate for the patient when the heart rate variation is at a second heart rate variation value that is less than the first heart rate variation value.

Example 11 can include, or can optionally be combined with the subject matter of one or any combination of Examples 1 through 10 to optionally include, the data input circuit configured to receive a cardiac activity signal that includes information about atrial contractions of the patient's heart. In Example 11, the processor circuit can be configured to determine the heart rate variation using the received cardiac activity signal that includes information about atrial contractions.

Example 12 can include, or can optionally be combined with the subject matter of one or any combination of Examples 1 through 11 to optionally include, the processor circuit configured to adjust a patient therapy using the computed patient metric.

Example 13 can include, or can optionally be combined with the subject matter of one or any combination of Examples 1 through 12 to optionally include, the processor circuit configured to initiate or adjust a rate-responsive pacing mode in a pacemaker in response to the determined heart rate variation.

Example 14 can include, or can optionally be combined with the subject matter of one or any combination of Examples 1 through 13 to optionally include, the processor circuit configured to adjust, in response to the determined heart rate variation, at least one of a maximum pacing rate that controls a maximum rate at which a pacemaker supplies pacing energy to a heart; a lower rate limit that controls at which heart rate a pacemaker begins to supply pacing energy to a heart; a patient exertion level threshold that controls at which patient physical activity level a pacing energy is initiated or adjusted; a rate-response reaction time that controls how quickly a pacing rate increases; a rate-response response factor that controls a pacing rate as a function of a patient exertion level; or a rate-response recovery time that controls a rate at which a pacing rate decreases from a maximum pacing rate to a lower rate limit when a patient exertion level is less than a specified threshold physical activity level.

Example 15 can include, or can optionally be combined with the subject matter of one or any combination of Examples 1 through 14 to optionally include, a patient posture sensor. In Example 15, the processor circuit can be configured to adjust the computed patient metric using the determined heart rate variation and information received from the patient posture sensor.

Example 16 can include, or can optionally be combined with the subject matter of one or any combination of Examples 1 through 15 to optionally include, the processor circuit configured to automatically provide a recommendation for a cardiac rhythm management device using the determined heart rate variation.

Example 17 can include, or can optionally be combined with the subject matter of one or any combination of Examples 1 through 16 to optionally include, subject matter (such as an apparatus, a method, a means for performing acts, or a machine readable medium including instructions that, when performed by the machine, that can cause the machine to perform acts), such as can include obtaining patient heart rate information including information about both intrinsic and non-intrinsic patient heart beats, determining a heart rate variation using the patient heart rate information including information about both intrinsic and non-intrinsic patient heart beats, the heart rate variation indicative of a number of both intrinsic and non-intrinsic patient heart beats within a specified heart rate range, and computing a patient metric using the determined heart rate variation indicative of a number of both intrinsic and non-intrinsic patient heart beats within a specified heart rate range.

Example 18 can include, or can optionally be combined with the subject matter of Example 17 to optionally include, determining a rate-responsive pacing mode suitability indication for the patient, the rate responsive pacing mode capable of automatically adjusting a pacing rate in response to a variation in a physiologic sensor output indicating a variation in the patient's metabolic need for a particular level of cardiac output.

Example 19 can include, or can optionally be combined with the subject matter of one or any combination of Examples 17 or 18 to optionally include, providing a predictive patient mortality indication using the determined heart rate variation.

Example 20 can include, or can optionally be combined with the subject matter of one or any combination of Examples 1 through 19 to optionally include, subject matter (such as an apparatus, a method, a means for performing acts, or a machine readable medium including instructions that, when performed by the machine, that can cause the machine to perform acts), such as can include a data input circuit configured to receive information indicative of a patient heart rate including information about both intrinsic and non-intrinsic patient heart beats, a memory circuit configured to store information about the patient heart rate over time, and a processor circuit, such as coupled to the memory circuit. In Example 20, the processor circuit can be configured to determine a heart rate variation using the stored information about the patient heart rate over time, the determined heart rate variation indicative of a number of both intrinsic and non-intrinsic patient heart beats within a specified heart rate range, and compute a predictive patient mortality indication using the determined heart rate variation, including identifying a lesser patient mortality rate for the patient when the heart rate variation is at a first heart rate variation value, and identifying a greater patient mortality rate for the patient when the heart rate variation is at a second heart rate variation value that is less than the first heart rate variation value.

Example 21 can include, or can optionally be combined with the subject matter of one or any combination of Examples 1 through 20 to optionally include, subject matter (such as an apparatus, a method, a means for performing acts, or a machine readable medium including instructions that, when performed by the machine, that can cause the machine to perform acts), such as can include a data input circuit configured to receive a cardiac activity signal of a patient, the cardiac activity signal including information about intrinsic and non-intrinsic cardiac activity, a memory circuit configured to store information about the received cardiac activity signal, and a processor circuit, such as coupled to the memory circuit. In Example 21, the processor circuit can be configured to determine a heart rate variability using the stored information about the cardiac activity signal including information about intrinsic and non-intrinsic cardiac activity, and/or determine a rate-responsive pacing mode suitability indication for the patient using the determined heart rate variability.

Example 22 can include, or can optionally be combined with the subject matter of Example 21 to optionally include, the processor circuit configured to determine the heart rate variability using patient heart rate information obtained from the stored information about the cardiac activity signal, including using patient heart rate information that includes information about both intrinsic and non-intrinsic patient heart beats, wherein the heart rate variability is indicative of a number of both intrinsic and non-intrinsic patient heart beats within a specified heart rate range.

Example 23 can include, or can optionally be combined with the subject matter of one or any combination of Examples 21 or 22 to optionally include, the processor circuit configured to compute a patient metric using the determined heart rate variability.

Example 24 can include, or can optionally be combined with the subject matter of one or any combination of Examples 21 through 23 to optionally include, the processor circuit configured to identify a lesser suitability for the rate-responsive pacing mode for the patient when the heart rate variability is at a first heart rate variability value, and identify a greater suitability for the rate-responsive pacing mode for the patient when the heart rate variability is at a second heart rate variability value that is less than the first heart rate variability value.

Example 25 can include, or can optionally be combined with the subject matter of one or any combination of Examples 21 through 24 to optionally include, the processor circuit configured to determine whether a count of the patient's non-intrinsic heart beats exceeds a specified portion of a total count of the patient's intrinsic and non-intrinsic heart beats during a specified period, and, when the count of the patient's non-intrinsic heart beats exceeds the specified portion of the total count of the patient's intrinsic and non-intrinsic heart beats during the specified period, determine the rate-responsive pacing mode suitability indication for the patient.

Example 26 can include, or can optionally be combined with the subject matter of one or any combination of Examples 21 through 25 to optionally include, a physiologic sensor configured to provide a signal indicative of the patient's metabolic need for a particular level of cardiac output, wherein the rate-responsive pacing mode is capable of automatically adjusting a patient pacing rate as a function of a variation in the signal indicative of the patient's metabolic need for the particular level of cardiac output. In Example 26, the physiologic sensor can include a patient physical activity level sensor, and/or an impedance sensor, such as can be configured to receive information about a thoracic or other impedance.

Example 27 can include, or can optionally be combined with the subject matter of one or any combination of Examples 21 through 26 to optionally include, a posture detection circuit configured to provide a signal indicative of a patient posture. In Example 27, the processor circuit can be configured to determine the rate-responsive pacing mode suitability indication for the patient using the determined heart rate variability and the signal indicative of a patient posture.

Example 28 can include, or can optionally be combined with the subject matter of one or any combination of Examples 21 through 27 to optionally include, the memory circuit configured to store patient heart rate information, such as obtained from the received cardiac activity signal, in a heart rate histogram bin corresponding to a patient heart rate range. In Example 28, the processor circuit can be configured to determine the heart rate variability using information about the heart rate histogram.

Example 29 can include, or can optionally be combined with the subject matter of Example 28 to optionally include, the processor circuit configured to determine the heart rate variability using a morphology or geometric characteristic of the heart rate histogram.

Example 30 can include, or can optionally be combined with the subject matter of one or any combination of Examples 21 through 29 to optionally include, the processor circuit configured to compute a predictive patient mortality indication using the determined heart rate variability.

Example 31 can include, or can optionally be combined with the subject matter of Example 30 to optionally include, the processor circuit configured to identify a lesser patient mortality rate for the patient when the heart rate variability is at a first heart rate variability value, and identify a greater patient mortality rate for the patient when the heart rate variability is at a second heart rate variability value that is less than the first heart rate variability value.

Example 32 can include, or can optionally be combined with the subject matter of one or any combination of Examples 21 through 31 to optionally include, the processor circuit configured to adjust a patient therapy using the determined heart rate variability.

Example 33 can include, or can optionally be combined with the subject matter of one or any combination of Examples 21 through 32 to optionally include, the processor circuit configured to initiate or adjust a rate-responsive pacing mode in a pacemaker in response to the determined heart rate variability.

Example 34 can include, or can optionally be combined with the subject matter of one or any combination of Examples 21 through 33 to optionally include, the processor circuit configured to adjust, in response to the determined heart rate variability, at least one of: a maximum pacing rate that controls a maximum rate at which a pacemaker supplies pacing energy to a heart; a lower rate limit that controls at which heart rate a pacemaker begins to supply pacing energy to a heart; a patient physical activity level threshold that controls at which patient physical activity level a pacing energy is initiated or adjusted; a rate-response reaction time that controls how quickly a pacing rate increases; a rate-response response factor that controls a pacing rate as a function of a patient physical activity level; or a rate-response recovery time that controls a rate at which a pacing rate decreases from a maximum pacing rate to a lower rate limit when a patient physical activity level is less than a specified threshold physical activity level.

Example 35 can include, or can optionally be combined with the subject matter of one or any combination of Examples 21 through 34 to optionally include, the processor circuit configured to automatically provide a recommendation for a cardiac rhythm management device using the determined heart rate variability.

Example 36 can include, or can optionally be combined with the subject matter of one or any combination of Examples 1 through 35 to optionally include, subject matter (such as an apparatus, a method, a means for performing acts, or a machine readable medium including instructions that, when performed by the machine, that can cause the machine to perform acts), such as can include obtaining heart rate variability of a patient, including information about both intrinsic and non-intrinsic patient cardiac activity, analyzing the heart rate variability using a processing device, and using the analysis of the heart rate variability, determining, using the processing device, a rate-responsive pacing mode suitability indication for the patient.

Example 37 can include, or can optionally be combined with the subject matter of Example 36 to optionally include programming an operating mode of an ambulatory cardiac function management device using the determined rate-responsive pacing mode suitability indication. In Example 37, using the analysis of the heart rate variability can include identifying a lesser suitability for a rate-responsive pacing mode for the patient when the heart rate variability is at a first heart rate variability value, and identifying a greater suitability for the rate-responsive pacing mode for the patient when the heart rate variability is at a second heart rate variability value that is less than the first heart rate variability value.

Example 38 can include, or can optionally be combined with the subject matter of Example 36 to optionally include, determining the rate-responsive pacing mode suitability indication for the subject when the analysis of the heart rate variability indicates that, during a specified period, a count of the subject's non-intrinsic heart beats exceeds a specified portion of a total count of the subject's intrinsic and non-intrinsic heart beats.

Example 39 can include, or can optionally be combined with the subject matter of one or any combination of Examples 36 through 38 to optionally include, providing a predictive patient mortality indication using the determined heart rate variability.

Example 40 can include, or can optionally be combined with the subject matter of one or any combination of Examples 1 through 39 to optionally include, subject matter (such as an apparatus, a method, a means for performing acts, or a machine readable medium including instructions that, when performed by the machine, that can cause the machine to perform acts), such as can include a data input circuit configured to receive information indicative of a patient heart rate including information about both intrinsic and non-intrinsic patient heart beats, a memory circuit configured to store information about the patient heart rate over time, and a processor circuit, such as coupled to the memory circuit. In Example 40, the processor circuit can be configured to determine a heart rate variability using the stored information about the patient heart rate over time, the determined heart rate variability indicative of a number of both intrinsic and non-intrinsic patient heart beats within a specified heart rate range. In Example 40, the processor circuit can be configured to determine a rate-responsive pacing mode suitability indication for the patient using the determined heart rate variability, including identifying a lesser suitability for the rate-responsive pacing mode for the patient when the heart rate variability is at a first heart rate variability value, and identifying a greater suitability for the rate-responsive pacing mode for the patient when the heart rate variability is at a second heart rate variability value that is less than the first heart rate variability value. In Example 40, the processor circuit can be configured to update a rate-responsive pacing mode in a pacemaker using the determined rate-responsive pacing mode suitability indication.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for determining whether to provide a rate-responsive pacing therapy or a non-rate-responsive pacing therapy to a patient, the apparatus comprising:
   a data input circuit configured to receive a cardiac activity signal of a patient, the cardiac activity signal including information about intrinsic and non-intrinsic cardiac activity;
   a memory circuit configured to store information about the received cardiac activity signal; and
   a processor circuit, coupled to the memory circuit, the processor circuit configured to:
   determine a heart rate variability using the stored information about the cardiac activity signal including information about intrinsic and non-intrinsic cardiac activity;
   determine a suitability indication configured to indicate whether to provide a rate-responsive pacing therapy to the patient instead of a non-rate-responsive pacing therapy, the suitability indication based on a characteristic of the determined heart rate variability; and
   at least one of:
   update, via a telemetry circuit, a therapy mode in a therapy delivery circuit to deliver either the rate-responsive or non-rate-responsive pacing therapy to the patient based on the suitability indication; and
   communicate, via the telemetry circuit, a recommendation to a caregiver using an external programmer that is communicatively coupled to the apparatus, the recommendation for delivering either the rate-responsive or non-rate-responsive pacing therapy to the patient based on the suitability indication.

2. The apparatus of claim 1, wherein the processor circuit is configured to determine the heart rate variability using patient heart rate information obtained from the stored information about the cardiac activity signal, including using patient heart rate information that includes information about both intrinsic and non-intrinsic patient heart beats, wherein the heart rate variability is indicative of a number of both intrinsic and non-intrinsic patient heart beats within a specified heart rate range.

3. The apparatus of claim 1, wherein the processor circuit is configured to compute a patient metric using the determined heart rate variability.

4. The apparatus of claim 1, wherein the processor circuit is configured to variability is at a first heart rate variability value, and identify a greater suitability for the rate-responsive pacing mode for the patient when the heart rate variability is at a second heart rate variability value that is less than the first heart rate variability value.

5. The apparatus of claim 1, wherein the processor circuit is configured to determine whether a count of the patient's non-intrinsic heart beats exceeds a specified portion of a total count of the patient's intrinsic and non-intrinsic heart beats during a specified period, and, when the count of the patient's non-intrinsic heart beats exceeds the specified portion of the total count of the patient's intrinsic and non-intrinsic heart beats during the specified period, determine the rate-responsive pacing mode suitability indication for the patient.

6. The apparatus of claim 1, comprising a physiologic sensor configured to provide a signal indicative of the patient's metabolic need for a particular level of cardiac output, wherein the rate-responsive pacing mode is capable of automatically adjusting a patient pacing rate as a function of a variation in the signal indicative of the patient's metabolic need for the particular level of cardiac output, wherein the physiologic sensor comprises at least one of a patient physical activity level sensor or an impedance sensor.

7. The apparatus of claim 1, comprising a posture detection circuit configured to provide a signal indicative of a patient posture, wherein the processor circuit is configured to determine the rate-responsive pacing mode suitability indication for the patient using the determined heart rate variability and the signal indicative of a patient posture.

8. The apparatus of claim 1, wherein the memory circuit is configured to store patient heart rate information, obtained from the received cardiac activity signal, in a heart rate histogram bin corresponding to a patient heart rate range; and
wherein the processor circuit is configured to determine the heart rate variability using information about the heart rate histogram.

9. The apparatus of claim 8, wherein the processor circuit is configured to determine the heart rate variability using a morphology characteristic of the heart rate histogram.

10. The apparatus of claim 1, wherein the processor circuit is configured to compute a predictive patient mortality indication using the characteristic of the determined heart rate variability.

11. The apparatus of claim 10, wherein the processor circuit is configured to identify a lesser patient mortality rate for the patient when the heart rate variability is at a first heart rate variability value, and identify a greater patient mortality rate for the patient when the heart rate variability is at a second heart rate variability value that is less than the first heart rate variability value.

12. The apparatus of claim 1, wherein the processor circuit is configured to adjust a patient therapy using the determined heart rate variability.

13. The apparatus of claim 1, wherein the processor circuit is configured to initiate or adjust a rate-responsive pacing mode in a pacemaker in response to the determined heart rate variability.

14. The apparatus of claim 1, wherein the processor circuit is configured to adjust, in response to the determined heart rate variability, at least one of:
a maximum pacing rate that controls a maximum rate at which a pacemaker supplies pacing energy to a heart;
a lower rate limit that controls at which heart rate a pacemaker begins to supply pacing energy to a heart;
a patient physical activity level threshold that controls at which patient physical activity level a pacing energy is initiated or adjusted;
a rate-response reaction time that controls how quickly a pacing rate increases;
a rate-response response factor that controls a pacing rate as a function of a patient physical activity level; or
a rate-response recovery time that controls a rate at which a pacing rate decreases from a maximum pacing rate to a tower rate limit when a patient physical activity level is less than a specified threshold physical activity level.

15. The apparatus of claim 1, wherein the processor circuit is configured to automatically provide a recommendation for a cardiac rhythm management device using the determined heart rate variability.

16. A method for choosing whether to provide a rate-responsive pacing therapy or a non-rate-responsive pacing therapy to a patient, the method comprising:
obtaining heart rate variability of a patient, including information about both intrinsic and non-intrinsic patient cardiac activity;
analyzing the heart rate variability using a processing device to determine a heart rate variability index that is characteristic of the heart rate variability;
based on the variability index, determining, using the processing device, a suitability indication configured to indicate whether to provide a rate-responsive pacing therapy to the patient instead of a non-rate-responsive pacing therapy; and
updating a therapy mode in a therapy delivery circuit in a pacemaker to deliver either the rate-responsive or non-rate-responsive pacing therapy to the patient based on the determined suitability indication.

17. The method of claim 16, wherein the using the variability index comprises identifying a lesser suitability for a rate-responsive pacing mode for the patient when the heart rate variability is at a first heart rate variability value, and identifying a greater suitability for the rate-responsive pacing mode for the patient when the heart rate variability is at a second heart rate variability value that is less than the first heart rate variability value.

18. The method of claim 16, further comprising determining the suitability indication for the subject when the analysis of the heart rate variability indicates that, during a specified period, a count of the subject's non-intrinsic heart beats exceeds a specified portion of a total count of the subject's intrinsic and non-intrinsic heart beats.

19. The method of claim 16, further comprising providing a predictive patient mortality indication using the determined heart rate variability index.

20. An implantable medical device for determining whether to provide a rate-responsive pacing therapy or a non-rate-responsive pacing therapy to a patient, the apparatus comprising:
- a data input circuit configured to receive intra-beat cardiac activity information indicative of the patient's heart rate including information about both intrinsic and non-intrinsic heart beats;
- a memory circuit configured to store information about the patient's heart rate over time; and
- a processor circuit, coupled to the memory circuit, the processor circuit configured to:
- determine an intra-beat heart rate variability using the stored information about the patient's heart rate over time, the determined intra-beat heart rate variability indicative of a number of both intrinsic and non-intrinsic patient heart beats within a specified heart rate range; and
- determine a pacing mode for delivering a pacing therapy to the patient, including choosing one of a rate-responsive pacing mode or a non-rate-responsive pacing mode for the pacing therapy, the choosing the pacing mode based on the determined intra-beat heart rate variability, and including choosing the non-rate-responsive pacing mode when the intra-beat heart rate variability is at a first heart rate variability value, and choosing the rate-responsive pacing mode when the intra-beat heart rate variability is at a second heart rate variability value that is less than the first heart rate variability value;
- wherein the implantable medical device includes a therapy circuit operably connected to the processor circuit, and the therapy circuit is configured to deliver the pacing therapy based on the chosen one of the rate-responsive pacing mode and the non-rate-responsive pacing mode.

* * * * *